US012793851B1

(12) United States Patent
Maier et al.

(10) Patent No.: US 12,793,851 B1
(45) Date of Patent: Nov. 10, 2026

(54) SYSTEMS AND METHODS FOR RISK FACTOR PREDICTIVE MODELING WITH MODEL EXPLANATIONS

(71) Applicant: MASSACHUSETTS MUTUAL LIFE INSURANCE COMPANY, Springfield, MA (US)

(72) Inventors: Marc Maier, Springfield, MA (US); Shanshan Li, Springfield, MA (US); Hayley Carlotto, Springfield, MA (US); Indra Kumar, Springfield, MA (US)

(73) Assignee: Massachusetts Mutual Life Insurance Company, Springfield, MA (US)

( * ) Notice: Subject to any disclaimer, the term of this patent is extended or adjusted under 35 U.S.C. 154(b) by 175 days.

(21) Appl. No.: 18/343,225

(22) Filed: Jun. 28, 2023

Related U.S. Application Data

(63) Continuation of application No. 15/931,791, filed on May 14, 2020, now Pat. No. 11,710,564.

(Continued)

(51) Int. Cl.
*G16H 50/30* (2018.01)
*G06N 5/045* (2023.01)

(Continued)

(52) U.S. Cl.
CPC ............. *G16H 50/20* (2018.01); *G06N 5/045* (2013.01); *G06N 20/00* (2019.01); *G06Q 10/10* (2013.01);

(Continued)

(58) Field of Classification Search
CPC ........ G16H 50/20; G16H 50/30; G16H 50/70; G16H 20/10; G16H 10/20; G16H 10/60;

(Continued)

(56) References Cited

U.S. PATENT DOCUMENTS 8,521,568 B1 8/2013 Easley
11,257,574 B1 * 2/2022 Boussios ................ G06N 20/00

(Continued)

FOREIGN PATENT DOCUMENTS

WO WO-2015/084548 A1 6/2015
WO WO-2017/220140 A1 12/2017

OTHER PUBLICATIONS

Aggour, K. S.; Bonissone, P. P.; Cheetham, W. E.; and Messmer, R. P. 2006. Automating the underwriting of insurance applications. AI magazine 27(3):36; Sep. 2006; 15 pages.

(Continued)

*Primary Examiner* — Alaaeldin M. Elshaer
(74) *Attorney, Agent, or Firm* — Foley & Lardner LLP

(57) ABSTRACT

A suite of fluidless predictive machine learning models includes a fluidless mortality module, smoking propensity model, and prescription fills model. The fluidless machine learning models are trained against a corpus of historical underwriting applications of a sponsoring enterprise, including clinical data of historical applicants. Fluidless models are trained by application of a random forest ensemble including survival, regression, and classification models. The trained models produce high-resolution, individual mortality scores. A fluidless underwriting protocol runs these predictive models to assess mortality risk and other risk attributes of a fluidless application that excludes clinical data to determine whether to present an accelerated underwriting offer. If any of the fluidless predictive models determines a high risk target, the applicant is required to submit clinical data, and an explanation model generates an explanation file for user interpretability of any high risk model prediction and the adverse underwriting decision.

20 Claims, 9 Drawing Sheets

Related U.S. Application Data

(60) Provisional application No. 62/993,584, filed on Mar. 23, 2020, provisional application No. 62/899,543, filed on Sep. 12, 2019, provisional application No. 62/848,397, filed on May 15, 2019.

(51) Int. Cl.

| | |
|---|---|
| ***G06N 20/00*** | (2019.01) |
| ***G06Q 10/10*** | (2023.01) |
| ***G06Q 40/03*** | (2023.01) |
| ***G06Q 40/08*** | (2012.01) |
| ***G16H 20/10*** | (2018.01) |
| ***G16H 50/20*** | (2018.01) |
| ***G16H 50/70*** | (2018.01) |

(52) U.S. Cl.
CPC ............. *G06Q 40/03* (2023.01); *G06Q 40/08* (2013.01); *G16H 20/10* (2018.01); *G16H 50/30* (2018.01); *G16H 50/70* (2018.01)

(58) Field of Classification Search
CPC ........ G06N 20/00; G06N 5/045; G06N 99/00; G06Q 40/03; G06Q 10/10; G06Q 40/00
USPC .......................................... 705/2, 3; 706/1–3
See application file for complete search history.

(56) References Cited

U.S. PATENT DOCUMENTS

| | | | | |
|---|---|---|---|---|
| 2003/0037063 | A1 | 2/2003 | Schwartz | |
| 2003/0177032 | A1 | 9/2003 | Bonissone et al. | |
| 2007/0021987 | A1 | 1/2007 | Binns et al. | |
| 2008/0057590 | A1 | 3/2008 | Urdea et al. | |
| 2009/0204446 | A1 | 8/2009 | Simon et al. | |
| 2009/0265190 | A1 | 10/2009 | Ashley et al. | |
| 2012/0296455 | A1 | 11/2012 | Ohnemus et al. | |
| 2013/0173283 | A1 | 7/2013 | Morse et al. | |
| 2014/0172466 | A1 | 6/2014 | Kemp et al. | |
| 2015/0039351 | A1 | 2/2015 | Bell et al. | |
| 2015/0287143 | A1 | 10/2015 | Gabriel et al. | |
| 2015/0294420 | A1 | 10/2015 | Hu | |
| 2016/0048766 | A1* | 2/2016 | McMahon | G06Q 40/08 706/12 |
| 2016/0078195 | A1 | 3/2016 | Sarkar et al. | |
| 2016/0196394 | A1 | 7/2016 | Chanthasiriphan et al. | |
| 2017/0124662 | A1 | 5/2017 | Crabtree et al. | |
| 2019/0180379 | A1 | 6/2019 | Nayak et al. | |
| 2019/0180852 | A1* | 6/2019 | Jiao | G16H 50/20 |
| 2019/0220793 | A1 | 7/2019 | Saarenvirta | |
| 2019/0378210 | A1* | 12/2019 | Merrill | G06N 5/01 |
| 2020/0020040 | A1 | 1/2020 | Gokhale et al. | |
| 2020/0098048 | A1 | 3/2020 | Kuruvilla et al. | |
| 2020/0104876 | A1 | 4/2020 | Chintakindi et al. | |
| 2020/0160998 | A1* | 5/2020 | Ward | G06F 18/2185 |
| 2022/0391670 | A1* | 12/2022 | Dalli | G06N 5/045 |
| 2024/0386326 | A1 | 11/2024 | Clarence et al. | |
| 2025/0384341 | A1 | 12/2025 | Cella et al. | |
| 2026/0162004 | A1 | 6/2026 | Rogawski et al. | |

OTHER PUBLICATIONS

B. Letham, C. Rudin, T. H. McCormick, and D. Madigan; Interpretable classifers using rules and bayesian analysis: Building a better stroke prediction model. Annals of Applied Statistics; Apr. 2015; 22 pages.

Breiman, L. 2001. Random forests. Machine learning 45(1):5-32; Apr. 11, 2001; 11 pages.

Case, A., and Deaton, A. 2015. Rising morbidity and mortality in midlife among white non-hispanic Americans in the 21st century. Pmc. of the National Academy of Sciences 112(49): 15078-15083; Sep. 17, 2015; 6 pages.

Chen, T., and Guestrin, C. 2016. Xgboost: A scalable tree boosting system. In Proceedings of the Twenty-Second ACM SIGKDD In?ternational Conference on Knowledge Discovery and Data Mining, 785-794. ACM; Aug. 13, 2016; 10 pages.

Chokshi, D. A.; El-Sayed, A. M.; and Stine, N. W. 2015. J-shaped curves and public health. JAMA 314(13):1339-1340; Oct. 6, 2015; 2 pages.

Consumer Financial Protection Bureau. Consumer credit reports: A study of medical and non-medical collec?tions, https://files.consumerfinance.gov/f/201412 cfpb reports consumer-credit-medical-and-non-medical- collections.pdf, Dec. 2014; 53 pages.

Cox, D. R. 1972. Regression models and life-tables regression. Journal of the Royal Statistical Society, Series B 34:187-220; Mar. 8, 1972; 34 pages.

Cox, H. J.; Bhandari, S.; Rigby, A. S.; and Kilpatrick, E. S. 2008. Mortality at low and high estimated glomerular filtration rate values: A u-shaped curve. Nephron Clinical Practice 110(2):c67-c72; Feb. 19, 2008; 6 pages.

D. Sculley, Gary Holt, Daniel Golovin, Eugene Davydov, Todd Phillips, Dietmar Ebner, Vinay Chaudhary, Michael Young, Jean-Francois Crespo, and Dan Dennison. Hidden technical debt in machine learning systems. In Advances in Neural Information Processing Systems 28, pp. 2503-2511. 2015; Oct. 7, 2017; 9 pages.

David J Garrow. Toward a definitive history of Griggs v. Duke Power Co., Vand. L. Rev., 67:197, Jan. 22, 2014 41 pages.

Goldwasser, P., and Feldman, J. 1997. Association of serum albumin and mortality risk. Journal of Clinical Epidemiology 50(6):693-703; Feb. 3, 1997; 11 pages.

Guizhou Hu, Mortality Assessment Technology: A New Tool for Life Insurance Underwriting, on The Risk, vol. 18, No. 3, https://pdfs.semanticscholar.org/bac0/3b8a85bf89c7a7b65076c082632d2d325519.pdf, 2002, 9 pages.

Hemant Ishwaran, Udaya B Kogalur, Eiran Z Gorodeski, Andy J Minn, and Michael S Lauer. High-dimensional variable selection for survival data. Journal of the American Statistical Association, 105(489):205-217, Nov. 2008, 13 pages.

Hemant Ishwaran, Udaya B Kogalur, Eugene H Blackstone, and Michael S Lauer. Random Survival Forests. The Annals of Applied Statistics, 2(3):841-860; Mar. 2008, 22 pages.

John Karlen. climbeR: "Calculate Average Minimal Depth of a Maximal Subtree for 'ranger' Package Forests"; https://CRAN.R-project.org/package=climbeR. R package version 0.0.1, Nov. 19, 2016; 8 pages.

Kalben, B. B. 2000. Why men die younger: Causes of mortality differences by sex. N. Am. Actuarial Journal 4(4):83-111; Jan. 4, 2013; 30 pages.

Kaplan, E. L., and Meier, p. 1958. Nonparametric estimation from incomplete observations. Journal of the American Statistical Association 53(282):457-481; Jun. 1958; 25 pages.

Katzman, J.; Shaham, U.; Bates, J.; Cloninger, A.; Jiang, T.; and Kluger, Y. 2016. Deep survival: A deep cox proportional hazards network. arXiv preprint arXiv: 1606.00931; Jun. 2016; 11 pages.

Kronmal, R. A.; Cain, K. C.; Ye, Z.; and Omenn, G. S. 1993. Total serum cholesterol levels and mortality risk as a function of age: A report based on the Framingham data. Archives of Internal Medicine 153 (9):1065-1073; May 10, 1993; 9 pages.

Lipton, Z. C. 2016. The mythos of model interpretability. In Proceedings of the ICML Workshop on Human Interpretability in Machine Learning, 96-100; Jun. 10, 2016; 5 pages.

Lundberg, Scott M, Gabriel G Erion, and Su-In Lee .; "Consistent Individualized Feature Attribution for Tree Ensembles." arXiv Preprint arXiv:1802.03888.; Feb. 12, 2018; 9 pages.

Marc Maier, Hayley Carlotto, Freddie Sanchez, Sherriff Balogun, Sears Merritt; "Transforming Underwriting in the Life Insurance Industry"; Proceedings of the Thirty-Third AAAI Conference on Artificial Intelligence, vol. 33 (2019):; Jul. 17, 2019; 8 pages.

Mike Batty et al., Predictive Modeling for Life Insurance: Ways Life Insurance can participate in the Business Analytics Revolution, Deloitte Consulting LLP, Apr. 2010, 22 pages.

National Association of Insurance Commissioners. Credit-based insurance scores, 2018. https://www.naic.org/cipr topics/topic credit based insurance score.htm , last updated Dec. 7, 2018, 3 pages.

(56) References Cited

OTHER PUBLICATIONS

Peter WF Wilson, Ralph B D'Agostino, Daniel Levy, Albert M Belanger, Halit Silbershatz, and William B Kannel. Prediction of coronary heart disease using risk factor categories. Circulation, 97(18):1837-1847, May 1998; 11 pages.
Phillip Janz et al., "The Impact on Relative Mortality and Prevalence from Triage in an Accelerated Underwriting Program", Reinsurance News, Jul. 2019, 5 pages.
Ranganath, R.; Perotte, A.; Elhadad, N.; and Blei, D.; Deep survival analysis. arXiv preprint arXiv:1608.02158; Aug. 6, 2016; 13 pages.
Ribeiro, M. T.; Singh, S.; and Guestrin, C.; Why should I trust you ?: Explaining the predictions of any classifier. In Proceedings of the Tventy-Second ACM SIGKDD International Conference on Knowledge Discovery and Data Mining, 1135-1144. ACM; Feb. 16, 2016; 10 pages.
Richard Wright, Mark Ellis, Steven R Holloway, and Sandy Wong. Patterns of racial diversity and segregation in the united states: 1990-2010. The Professional Geographer, 66(2):173-182, https://europepmc.org/articles/pmc4114976, Jan. 2013; 17 pages.
Robert Chen et al., "Patient Stratification Using Electronic Health Records from a Chronic Disease Management Program", IEEE J Biomed Health Inform., Author manuscript; available in PMC Jul. 4, 2017.
Ronen Avraham, Kyle D Logue, and Daniel Schwarcz. Understanding insurance antidiscrimination law. S. Cal. L. Rev., 87:195, Jan. 2014; 81 pages.
Rosinger, A.; Carroll, M. D.; Lacher, D.; and Ogden, C. 2017. Trends in total Cholesterol, Triglycerides, and Low-density Lipoprotein in US Adults, 1999-2014. JAMA Cardiology 2(3):339-341; Mar. 2017; 3 pages.
Scism, L. 2017. New York regulator seeks details from life insurers using algorithms to issue policies. The Wall Street Journal; Jun. 29, 2017; 2 pages.
Scott M Lundberg and Su-In Lee. A unified approach to interpreting model predictions. In I. Guyon, U. V. Luxburg, S. Bengio, H. Wallach, R. Fergus, S. Vishwanathan, and R. Garnett, editors, Advances in Neural Information Processing Systems 30, pp. 4765-4774. Curran Associates, Inc., http://papers.nips.cc/paper/7062- a-unified- approach-to- interpreting-model-predictions.pdf, May 22, 2017; 10 pages.
Wright, M. N., and Ziegler, A. 2017. ranger: A fast implementation of random forests for high dimensional data in C++ and R. Journal of Statistical Software 77(1): Mar. 1-17, 2017; 17 pages.
Napa et al., "Comparative analysis of explainable machine learning models for cardiovascular risk stratifcation using clinical data and shapley additive explanations", Intelligence-Based Medicine, Aug. 12, 2025, 100286, 12 pages.

* cited by examiner

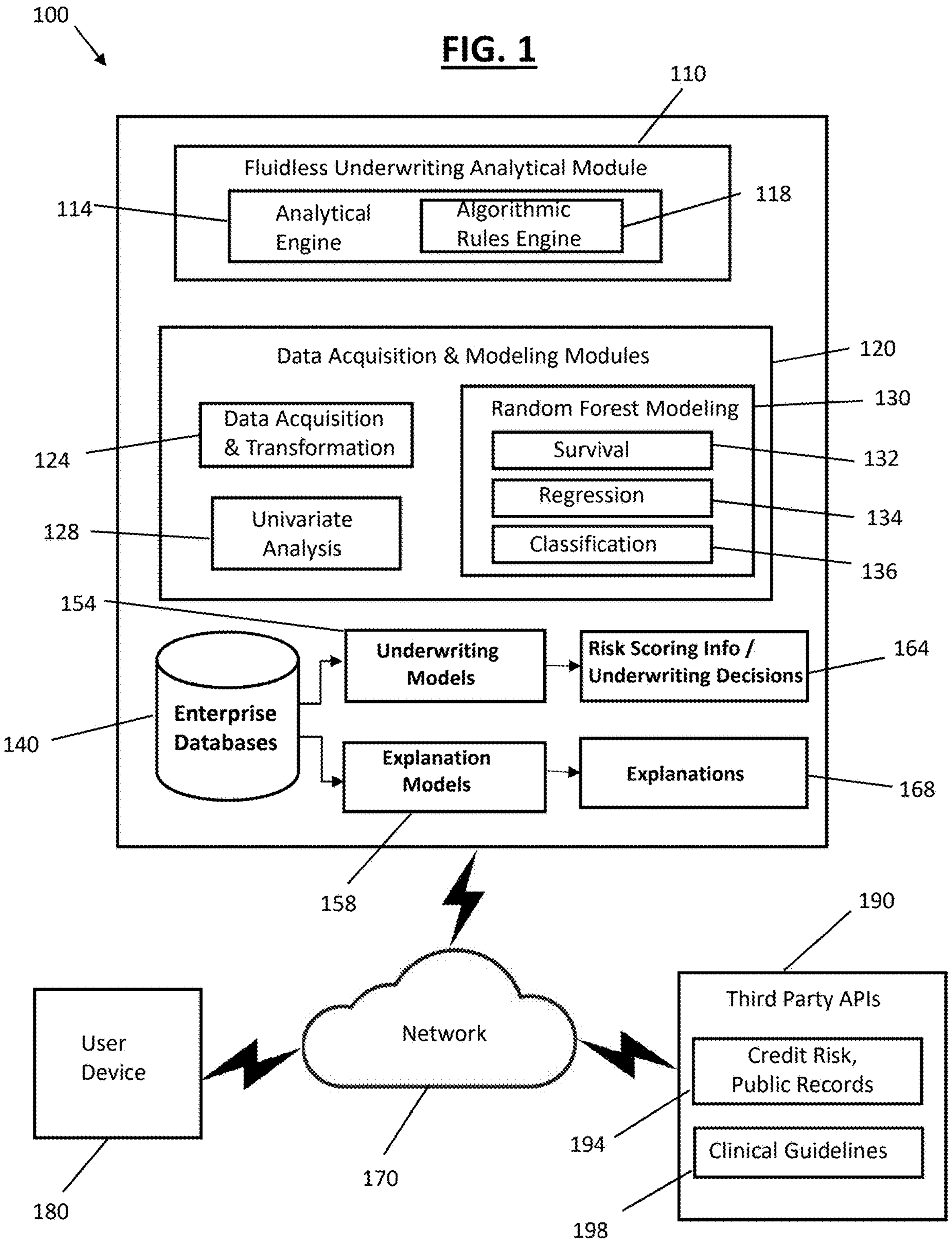
100
FIG. 1
110
Fluidless Underwriting Analytical Module
114
Analytical Engine
Algorithmic Rules Engine
118
Data Acquisition & Modeling Modules
120
Random Forest Modeling
130
124
Data Acquisition & Transformation
Survival
132
Regression
134
128
Univariate Analysis
Classification
136
154
Underwriting Models
Risk Scoring Info / Underwriting Decisions
164
140
Enterprise Databases
Explanation Models
Explanations
168
158
190
Third Party APIs
User Device
Network
Credit Risk, Public Records
194
Clinical Guidelines
170
180
198

SYSTEMS AND METHODS FOR RISK FACTOR PREDICTIVE MODELING WITH MODEL EXPLANATIONS

CROSS-REFERENCE TO RELATED APPLICATIONS

The present application is a continuation application of Ser. No. 15/931,791, filed May 14, 2020, which claims benefit of U.S. Provisional App. No. 62/848,397, filed May 15, 2019, claims the benefit of U.S. Provisional App. No. 62/899,543, filed Sep. 12, 2019, and claims the benefit of U.S. Provisional App. No. 62/993,584 filed Mar. 23, 2020, all of which are incorporated by reference in their entirety.

TECHNICAL FIELD

The present disclosure relates generally to predictive modeling.

BACKGROUND

With the advent of machine learning techniques, algorithmic systems can be quite complex. The algorithmic systems do not provide adequate transparency into factors affecting decisions and scoring. Additionally, from a user's standpoint, algorithmic processing can be opaque, e.g., a black box process in which the user enters items of information just to see the computer system produce a result. In determining whether to train a model, revise an algorithm, or deploy a new model, more insight is needed into the critical factors affecting the output of the model. It can be very difficult to explain decisions resulting from a machine learning model to affected users in a way that allows users to trust the algorithmic processing. Understanding the reasons behind model predictions is desirable.

SUMMARY

What is needed are systems and methods that provide qualitative understanding and quantitative understanding of underwriting model predictions. Another need is for systems and methods that provide persons affected by underwriting decisions with a specific reason or reasons for any adverse underwriting decision. An additional need is systems and methods that provide qualitative understanding and quantitative understanding of algorithmic underwriting models for enterprise users of these models, such as underwriters and developers. An additional need is for a tool to enable model developers to check algorithmic underwriting models for inconsistencies and undesirable behavior.

Embodiments described herein can improve customer experience with faster processing and reduced customer burdens of providing information required by the underwriting process, while providing fair and transparent algorithmic underwriting. A fluidless underwriting model suite for predictive modeling of mortality treats clinical assessment data as excluded risk factors while enabling assessment and classification of risk with respect to applicants for life insurance according to acceptable alternative criteria. The fluidless underwriting protocol generates and displays explanations of model outputs including predictions and underwriting decisions.

In an embodiment, a processor-based method receives from a user device a plurality of variables of an electronic application to an enterprise, wherein the plurality of variables for the electronic application exclude clinical data for an applicant of the electronic application. Upon receiving the plurality of variables for the electronic application from the user device, the processor retrieves public data identified with the applicant from one or more third-party sources. The processor executes a first predictive machine learning module configured to determine a first risk rank representative of a mortality risk for the electronic application and to classify the electronic application into one of a first high risk group and a first low risk group based upon the first risk rank. In various embodiments, the first predictive machine learning module comprises a machine learning model utilizing one or more of survival modeling, regression modeling, and classification modeling. The processor executes a second predictive machine learning module configured to determine a second risk rank and to classify the electronic application into one of a second high risk group and a second low risk group based upon the second risk rank. The processor executes a third predictive machine learning module configured to determine a third risk rank and to classify the electronic application into one of a third high risk group and a third low risk group based upon the third risk rank.

In the event the processor classifies the electronic application into all of the first low risk group, the second low risk group, and the third low risk group, the processor generates a user interface for display of an accelerated application offer at the user device. In the event the processor classifies the electronic application into one or more of the first high risk group, the second high risk group, and the third high risk group, the processor generates a user interface for display at the user device of an explanation file including interpretability data for the predictive machine learning model prediction of the one or more of the first high risk group, the second high risk group, and the third high risk group.

In an embodiment, the method determines whether to generate the user interface for display of the accelerated application or to display an underwriting decision declining the fluidless application and instructing the applicant to submit clinical data in any resubmitted underwriting application.

In various embodiments, the processor executes an explanation model to generate an explanation file for the electronic application. The explanation file is a textual and/or visual artifact that provides a quantitative understanding and/or qualitative understanding of predictions by the machine learning model.

In various embodiments, the method inputs data associated with the electronic application into an additive feature attribution module in order to generate the explanation file of the predictive machine learning module outputs. Inputted data include features data representative of at least some of the variables of the electronic application, model object data representative of the machine learning model, and model prediction data representative of predictive machine learning module outputs. In an embodiment, the method generates a report for the electronic application for display by a user interface, the report including the quantitative score, underwriting decision data derived from the underwriting decision file, and explanation data derived from the explanation file for the electronic application.

In an embodiment, the additive feature attribution module executes a SHAP values (SHapley Additive exPlanation) algorithm. In an embodiment, the additive feature attribution module executes a Kernel SHAP algorithm. In an embodiment, the additive feature attribution module executes a Tree SHAP algorithm.

In an embodiment, each of a plurality of historical application records includes clinical assessment data for an applicant of the respective historical application record. Prior to inputting the historical application records into the machine learning model ensemble, the method supplements each historical application record with public data identified with the applicant of the respective historical application record. In an embodiment, the public data comprises public records and credit risk data. In various embodiments, the first predictive machine learning model is continuously trained using updated public records and credit data.

In various embodiments, the second risk rank is representative of a propensity of the applicant of the electronic application to be a smoker. In an embodiment, the second predictive machine learning module is a random forest classification model configured to estimate the propensity of the applicant of the electronic application to be a smoker.

In various embodiments, the third risk rank is representative of prescription drug data for the applicant of the electronic application. In an embodiment, the third predictive machine learning module is configured to determine disqualifying medical risks based on information derived from prescription drug fills for the applicant of the electronic application.

In an embodiment, the first risk rank comprises a quantitative score representative of the mortality risk for the electronic application. In various embodiments, one or more of the first risk rank, the second risk rank, and the third risk rank comprises a percentile within a score distribution for a population of customers of the enterprise.

In an embodiment, a method for processing an electronic application, comprises receiving, by a processor, a plurality of variables of an electronic application from a user device, wherein the plurality of variables for the electronic application exclude clinical data for an applicant; upon receiving the plurality of variables for the electronic application from the user device, retrieving, by the processor, public data identified with the applicant of the electronic application from one or more third-party sources; executing, by the processor, a first predictive machine learning module to determine a first risk rank representative of a mortality risk for the electronic application and to classify the electronic application into one of a first high risk group and a first low risk group based upon the first risk rank; executing, by the processor, a second predictive machine learning module to determine a second risk rank and to classify the electronic application into one of a second high risk group and a second low risk group based upon the second risk rank; executing, by the processor, a third predictive machine learning module to determine a third risk rank and to classify the electronic application into one of a third high risk group and a third low risk group based upon the third risk rank; and when the processor classifies the electronic application into one or more of the first high risk group, the second high risk group, and the third high risk group, generating, by the processor, an explanation file for display on a user interface, the explanation file including interpretability data based on the determination of the one or more of the first high risk group, the second high risk group, and the third high risk group.

In another embodiment, a system comprises an analytical engine containing a processor configured to execute a plurality of non-transitory computer-readable instructions configured to receive a plurality of variables for an electronic application from a user device that excludes clinical data for an applicant of the electronic application, and for retrieving public data identified with the applicant of the received electronic application from one or more third-party sources; execute a predictive machine learning module to determine a mortality risk rank for the electronic application and classify the electronic application into a first low risk group or a first high risk group; execute a smoking propensity predictive model; wherein the smoking propensity model is configured to estimate a propensity of the applicant of the electronic application to be a smoker and determine a smoking/non-smoking binary target; execute a prescription drug data predictive model configured to determine a disqualifying medical risk based on information derived from prescription drug fills for the applicant of the electronic application; and generate and presenting the user interface that displays information associated with an accelerated application offer when the analytical engine server classifies the electronic application into the first low risk group, determines the non-smoking binary target, and does not determine the disqualifying medical risk; and that displays an explanation file including interpretability data when the analytical engine server effects one or more of the following: classifies the electronic application into the first high risk group, determines the smoking binary target, determines the disqualifying medical risk.

Other objects, features, and advantages of the present disclosure will become apparent with reference to the drawings and detailed description of the illustrative embodiments that follow.

BRIEF DESCRIPTION OF THE DRAWINGS

Non-limiting embodiments of the present disclosure are described by way of example with reference to the accompanying figures which are schematic and are not intended to be drawn to scale. Unless indicated as representing the background art, the figures represent aspects of the disclosure.

FIG. 1 is a system architecture for a machine learning underwriting system including an explanation model, according to an embodiment.

DETAILED DESCRIPTION

Figure 2:
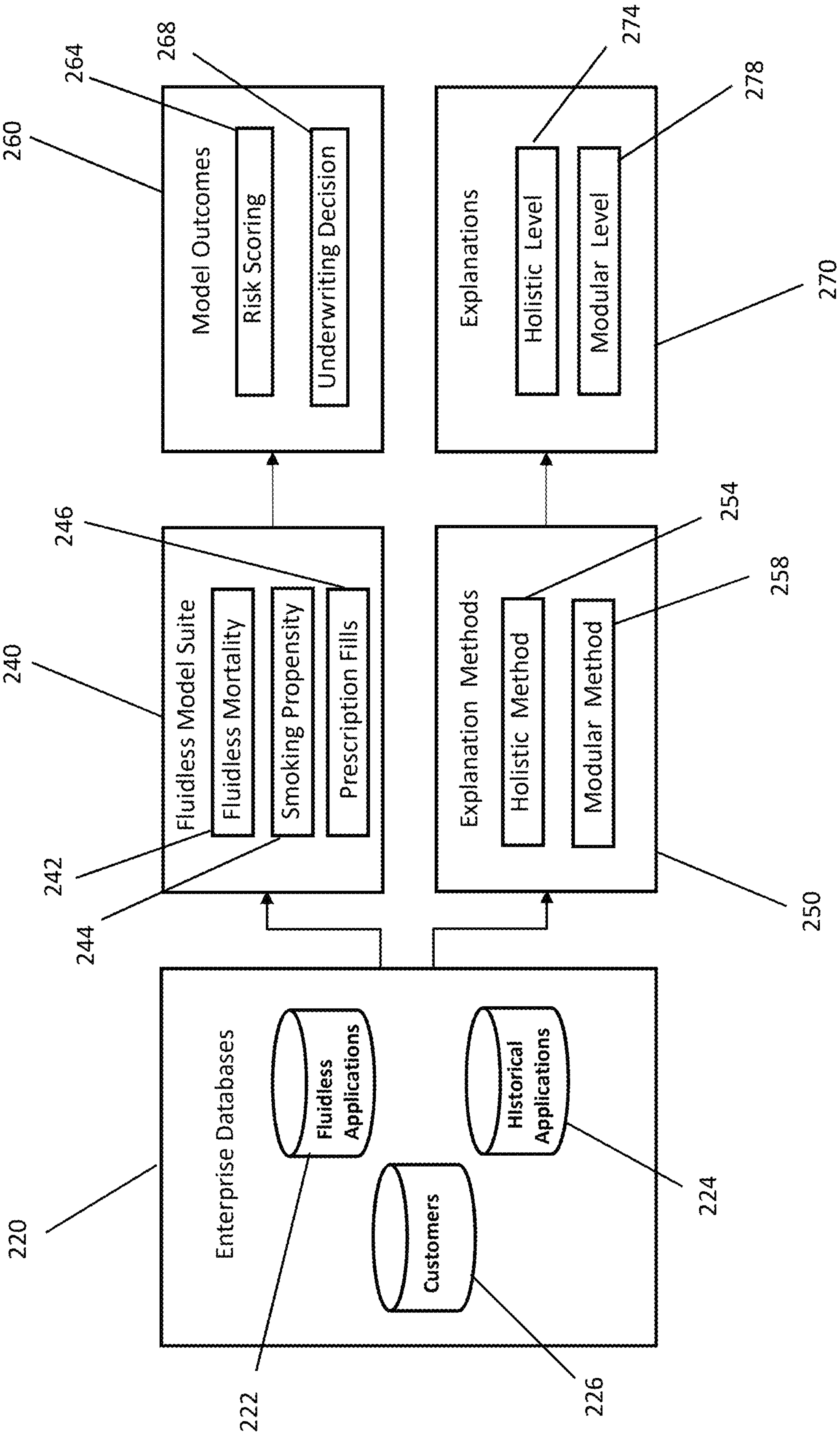
FIG. 2 is a schematic diagram of databases, models, and model outputs of a machine learning underwriting system with underwriting model suite and explanations, according to an embodiment.

In the following detailed description, reference is made to the accompanying drawings, which depict non-limiting, illustrative embodiments of the present disclosure. Other embodiments may be utilized and logical variations, e.g., structural and/or mechanical, may be implemented without departing from the scope of the present disclosure. To avoid unnecessary detail, certain information, items, or details known to those skilled in the art may be omitted from the following.

Underwriting is the process an insurance company uses to determine whether or not a potential customer is eligible for insurance, and what rate that potential customer should pay for the insurance if eligible. Insurance underwriting seeks to spread risk among a pool of insured in a manner that is both fair to the customer and profitable for the insurer. One consideration is that it does not make sense for insurers to sell life insurance, for example, to everyone who applies for it. Additionally, although insurance companies do not intend to charge their customers excessively high rates, it is not prudent for them to charge all their policyholders the same premium. Underwriting enables the company to decline coverage to certain applicants, and to charge the remaining applicants premiums and to provide other policy terms that are commensurate with their level of risk.

Traditionally, underwriting has been a manual process. Underwriting can involve numerous people including agents and doctors, and it can be very time-consuming. Therefore, various entities have developed systems and methods to automate the underwriting process in order to improve decision-making, reduce the number of people involved, and accelerate the underwriting process. These systems and methods may be referred to as algorithmic underwriting. With the advent of machine learning techniques, algorithmic underwriting systems can be quite complex. It can be challenging to describe the methodology that resulted in underwriting decisions, such as a decision to decline coverage, a decision to charge certain premiums, or a decision to impose a policy limitation. Therefore, it can be very difficult to explain underwriting decisions to affected customers in a way that these customers can trust the process. Understanding the reasons behind model predictions is quite important in assessing trust. Trust in individual model predictions is fundamental if one is affected by the model predictions.

Traditionally, most types of life insurance require an estimate of the expected lifetime of an individual at the time of application, commonly called the "mortality risk." Conventional protocols for collecting and analyzing data that describes mortality risk are known as underwriting. Actuaries compute the cost of covering mortality risk over the lifetime of the policy and translate it into a set of premium payments required throughout a policy's term. Life insurance risk assessment has primarily consisted of point systems developed by medical doctors and experienced underwriters. Such protocols commonly calculate risk by mapping medical and behavioral attributes to point values that either debit or credit an overall score. A life insurance underwriter reviews an application to calculate the net number of points and to determine one of several risk classes that determine pricing according to aggregate mortality.

The system and method of the present disclosure represent an underwriting protocol that improves customer experience with faster processing and reduced customer burdens of providing information required by the underwriting process. The underwriting protocol eliminates the traditional requirement in underwriting of life insurance products of collection of body fluids and various physical measurements, and analysis of risk factors based on these inputs. In the present disclosure, the underwriting protocol and the application received from the user are sometimes called "fluidless" (e.g., fluidless underwriting, fluidless application).

As used in the present disclosure, a "risk factor" is any variable associated with a health outcome or state, such as a risk of disease, infection and/or health-related event, e.g., a stroke, diabetes, heart attack, cancer and death. Risk factors may be correlated with a health outcome or state and may have a causal relationship with the health outcome or state. In the present disclosure, the omitted or excluded risk factors are risk factors derived from collection and analysis of body fluids and various biophysical measurements. In the present disclosure, these are sometimes called "clinical assessment risk factors" or alternatively "clinical assessments," and the collected medical data for these clinical assessments (e.g., body fluids and biophysical measurements) are sometimes called "clinical data," or alternatively "clinical laboratory data."

In lieu of clinical assessments as inputs to mortality predictions, the system and method of the present disclosure employ a mortality predictive model trained using data from a large corpus of historical applications based on traditional underwriting protocols, in conjunction with public data sources that can provide a thorough view of prospective customers. The system and methods of the present disclosure receive as input applications of prospective customers that exclude clinical data, and apply fluidless mortality predictive modeling to determine whether to approve sale to the applicant of a risk-pooling product, such as life insurance. If the fluidless underwriting protocol does not result in approval of the fluidless application, the applicant can submit clinical data in an application to be underwritten inclusive of those risk factors.

Clinical data collected in medical examinations in support of conventional applications for life insurance are typically employed to assess the applicant's health, to confirm information included in the application, and to screen for illegal drug use. Much of the collected clinical data is also obtained from other sources during the application process, and clinical test results and answers to examination questions are typically checked for consistency with the other sources.

Clinical laboratory data are a point-in-time view into an individual's health. Underwriting ties various clinical data to all-cause mortality predictions and to specific causes of mortality. Clinical assessments based on collected blood and urine samples typically test the collected fluids to screen for dozens of indicators of diseases and conditions (health indicators). Examples of clinical assessment risk factors include HIV and AIDS; sexually transmitted diseases (STD); cholesterol, (including LDL and HDL) and triglycerides (e.g., as indicators of heart disease risk factors); hemoglobin A1C, fructosamine and glucose levels (e.g., as indicators of diabetes); creatinine, hemoglobin and proteins (e.g., as indicators of kidney disease); and urine acidity (e.g., as indicator of impaired kidney function or diabetes). Typical medical examinations also screen for nicotine and cotinine in the urinalysis in order to determine tobacco usage. Additionally, clinical assessments may include biophysical examinations such as weighing the applicant and questioning the applicant, e.g., about lifestyle.

While excluding such clinical assessments eliminates informative indicators of risk factors that can yield substantial protective value in risk selection, the fluidless underwriting protocols of the present disclosure identify low-risk applicants for whom traditional clinical assessments can be waived with little to no impact on mortality risk. In lieu of clinical laboratory data, fluidless underwriting protocols disclosed herein utilize nontraditional data sources—public records and credit risk—that yield information on insurance applicants' behavior providing significant insights into mortality risk. In addition to those nontraditional data sources, fluidless underwriting protocols disclosed herein can include a client medical interview in the application process.

A fluidless underwriting protocol was validated by simulating a set of applications approved by the protocol, also herein called a "book of business." The simulation compared the book of business with historical underwriting risk class offers that effectively control all primary actuarial factors. This simulation showed that fluidless underwriting protocols incorporating the excluded risk-factor predictive modeling systems and methods of the present disclosure generate substantially improved offer rates based on accelerated underwriting without compromising mortality margins of conventional underwriting protocols.

The system and method of the present disclosure apply machine learning methods to underwriting protocols. Complex machine learning methods have become common in decision making systems in industry and government. When these methods are deployed in settings that affect human data subjects, an increasing concern of users and regulators is that they may have difficulty in oversight of mathematical tools. This has resulted in calls for greater transparency. In Europe, the General Data Protection Regulation gives individuals the right to "meaningful information about the logic involved" in algorithmic decision-making. In applying algorithmic decision-making methods in the life insurance industry, various regulatory authorities in the United States have required insurance companies to provide insured or potential insured with specific reasons for adverse underwriting decisions.

Underwriting protocols provide users such as underwriters, developers, and consumers with explanations for algorithmic underwriting outcomes. As used in the present disclosure, "explanations" are textual and visual artifacts that provide understanding of model predictions. An explanation can provide an understanding of an individual prediction of a machine learning model. The explanation can provide an understanding of the machine learning model itself. A machine learning model can provide quantitative predictions, and the explanation can provides one or both of qualitative understanding and quantitative understanding of the model's quantitative predictions. Explanations of machine learning models are commonly associated with "interpretability." As used herein, "interpretability" denotes the degree to which a human can understand the cause of a decision by a machine learning model. Properties of an interpretable model can include that a human can repeat the model's computation process with a full understanding of the algorithm.

As used in the present disclosure, an "explanation model," also herein called an "interpretability model," treats explanations of predictions of a machine learning model as a model itself. In various embodiments, an explanation model implements additive feature attribution for interpretability of underwriting model outcomes. Additive feature attribution provides various desirable properties in an explanation method. In various embodiments, an explanation model using additive feature explanation provides users with real-time explanations of underwriting model predictions. In various embodiments, an explanation model includes a transparency tool that enables users to easily visualize signals picked up by a machine learning underwriting model. Model developers can use the transparency tool in order to check a machine learning underwriting model for inconsistencies and undesirable behavior.

Disclosed embodiments of fluidless underwriting method apply a suite of predictive models to model inputs for a fluidless application in order to determine whether to present an accelerated underwriting offer to the applicant. In order to receive approval for presentation of an accelerated underwriting offer, the application must pass all model components of the fluidless model suite. In the event the application is declined, an explanation model generates one or both of a holistic explanation and a modular explanation for display to the applicant. As used in the present application, a "holistic" explanation is aimed at interpretability of the fluidless predictive model suite as a whole, including understanding the decision whether to present an accelerated underwriting offer to the applicant. As used in the present application, a "modular" explanation is aimed at interpretability of a prediction by a particular component model of the fluidless predictive model suite, e.g., in the event the application is declined because the application failed to pass that component model.

Disclosed embodiments of a fluidless underwriting method apply on demand a fluidless mortality predictive model that has been trained against a large corpus of historical underwriting applications including clinical assessment data. During model training the method executes a predictive machine learning model configured to determine a mortality score for each historical application record of a plurality of historical application records stored in a historical application database. The method effects feature transformations on various attributes of historical application records to construct engineered features with improved impacts on predicted value. Additionally, the predictive machine learning model effects a missingness procedure that provides imputed values for missing values in the historical application data. The predictive machine learning model is configured to determine the set of mortality scores by inputting engineered features and the customer profile data into a suite of predictive models based on survival, regression, and classification tasks. In an example, this suite of models uses the random forest algorithm.

FIG. 1 shows a system architecture for a fluidless application review system 100, also herein called a "fluidless underwriting system," of a sponsoring enterprise. The fluidless underwriting system 100 may be hosted on one or more computers (or servers), and the one or more computers may include or be communicatively coupled to one or more databases. The application review system 100 manages predictive modeling of mortality risk factors that exclude clinical assessment risk factors for applicants for life insurance or other financial products of the sponsoring enterprise.

A sponsoring enterprise for interpretable underwriting system 100 can be an insurance company or other financial services company, which may be represented by insurance agents or advisors. In some cases, an insurance agent may be associated with only a single insurance provider (sometimes referred to as a "captive" insurance agent). In other cases, an "independent" insurance agent, sometimes called an "insurance broker," may be associated with several different insurance providers. A user (customer or customer representative) can submit a digital application via user device 180, and the digital application received by interpretable underwriting system 100 can be assigned to an agent or advisor.

Fluidless underwriting analytical module 110 includes an analytical engine 114 and an algorithmic rules engine submodule 118. Example algorithmic rules engine submodule 118 executed thousands of automated rules encompassing health, behavioral, and financial attributes collected through digital fluidless applications 222 and through real-time vendor APIs 190. As used herein, a module may represent functionality (or at least a part of the functionality) performed by a server and/or a processor. For instance, different modules may represent different portion of the code executed by the analytical engine server to achieve the results described herein. Therefore, a single server may perform the functionality described as being performed by separate modules.

Analytical engine 114 can be executed by a server, one or more server computers, authorized client computing devices, smartphones, desktop computers, laptop computers, tablet computers, PDAs and other types of processor-controlled devices that receive, process, and/or transmit digital data. Analytical engine 114 can be implemented using a single-processor system including one processor, or a multi-processor system including any number of suitable processors that may be employed to provide for parallel and/or sequential execution of one or more portions of the techniques described herein. Analytical engine 114 performs these operations as a result of central processing unit executing software instructions contained within a computer-readable medium, such as within memory. In one embodiment, the software instructions of the system are read into memory associated with the analytical engine 114 from another memory location, such as from a storage device, or from another computing device via communication interface. In this embodiment, the software instructions contained within memory instruct the analytical engine 114 to perform processes described below. Alternatively, hardwired circuitry may be used in place of, or in combination with, software instructions to implement the processes described herein. Thus, implementations described herein are not limited to any specific combinations of hardware circuitry and software.

In various embodiments, underwriting models 154 apply machine learning predictive modeling to enterprise data 140 and to third-party data 190 to derive model outcomes 164. In various embodiments, model outcomes 164 include risk scoring information and underwriting decisions for users who have submitted a fluidless application for insurance. In various embodiments, underwriting decisions include an application decision for the fluidless application. In various embodiments, underwriting decisions include a decision to present an application offer file for the fluidless application. In various embodiments, underwriting decisions include a decision to decline to present an application offer file for the fluidless application.

In various embodiments, model outcomes 164 include risk scoring information, also herein called "risk ranks." Risk ranks may include, for example, quantitative risk scores, percentiles, binary risk outcomes, and risk classes. In an example, risk ranks include the user's percentile within the score distribution for a population of general users, together with the score of the particular user. Risk scoring can be a binary outcome, such as "pass" or "fail." Risk scores can define one or more bins as percentile ranges in a percentile distribution for a population of general users. Risk scoring can rank cases by the likelihood of belonging to one risk class or the other. Risk scoring can determine a quantitative risk score, such as net number of points, for the user and translates this risk score into one of several coarse-grained risk classes. Risk ranks can include a risk class to which the user has been assigned. For example, the user may be assigned to UPNT for non-smokers or SPT for self-reported smokers. In some cases, a sponsoring enterprise may deny coverage for an applicant with a risk rank representing a very high medical or financial risk.

In parallel with predictive modeling of underwriting, an explanation model 158, also herein called "explanation method" or "interpretability model," generates explanations 168, also herein called explanation files, of model outcomes. Explanation model 158 can generate an explanation file for display on user device 180. An explanation file displayed by user device can include interpretability data based on predictive machine learning modeling by underwriting models 154. Additionally, the displayed explanation file can include risk scoring information and underwriting decisions 164.

In the underwriting system embodiment of FIG. 2, enterprise databases 220 consist of various databases under custody of a sponsoring enterprise, including fluidless applications database 222, historical applications database 224, and customer database 226. Enterprise databases 220 are organized collections of data, stored in non-transitory machine-readable storage. The databases may execute or may be managed by database management systems (DBMS), which may be computer software applications that interact with users, other applications, and the database itself, to capture (e.g., store data, update data) and analyze data (e.g., query data, execute data analysis algorithms). In some cases, the DBMS may execute or facilitate the definition, creation, querying, updating, and/or administration of databases. The databases may conform to a well-known structural representational model, such as relational databases, object-oriented databases, and network databases. Example database management systems include MySQL, PostgreSQL, SQLite, Microsoft SQL Server, Microsoft Access, Oracle, SAP, dBASE, FoxPro, IBM DB2, LibreOffice Base, FileMaker Pro. Example database management systems also include NoSQL databases, i.e., non-relational or distributed databases that encompass various categories: key-value stores, document databases, wide-column databases, and graph databases.

A suite of fluidless models 240 includes a Fluidless Mortality Model 242, Smoking Propensity Model 244, and Prescription Fills Model 246. In an example, fluidless models 240 were trained against a large corpus of historical underwriting applications 226 of a sponsoring enterprise. With further reference to FIG. 1, data acquisition and transformations module 124 applied a data append procedure and data transformation procedures to the historical application data to yield an extensive data set with engineered features having improved predictive values. Fluidless models 240 were then trained by application of models within random forest survival models ensemble 130. Model training curated a data set on the scale of one million historical applications, wherein the historical applications included then-current clinical assessment data of the applicants. The trained models produced high-resolution, individual mortality scores.

In an example, historical underwriting applications 276 included data obtained from an extended time period. This presented the challenge in modeling of taking into account temporal factors, such as a decreasing trend of certain lab values over the time period of the historical applications. Example modeling techniques of the disclosure applied a statistical adjustment to account for covariate shift or non-stationarity, i.e., differences in distribution of certain predictive variables over the relevant time period.

In parallel with predictive modeling of underwriting, explanation methods 250, also herein called "explanation models" or "interpretability models," generate explanations 270 of model outcomes. Example methods 250 include holistic method 254, which generates holistic level explanations 274 of model outcomes, and modular method 258, which generates modular level explanations 278 of model outcomes.

Explanation methods incorporate additive feature attribution. Additive feature attributions describes the sensitivity of underwriting machine learning models 240 to different values in a rigorous manner. An example additive feature attributions module employs a SHAP values (SHapley Additive exPlanation) algorithm. The additive feature attribution module can execute a Kernel SHAP algorithm. The additive feature attribution module can execute a Tree SHAP algorithm. Additive feature attributions can generate explanations of various outputs of random forest survival models 240, including for example explanations of raw output of the tree model, output of the model transformed into probability space, and model performance metrics broken down by feature.

Figure 8:
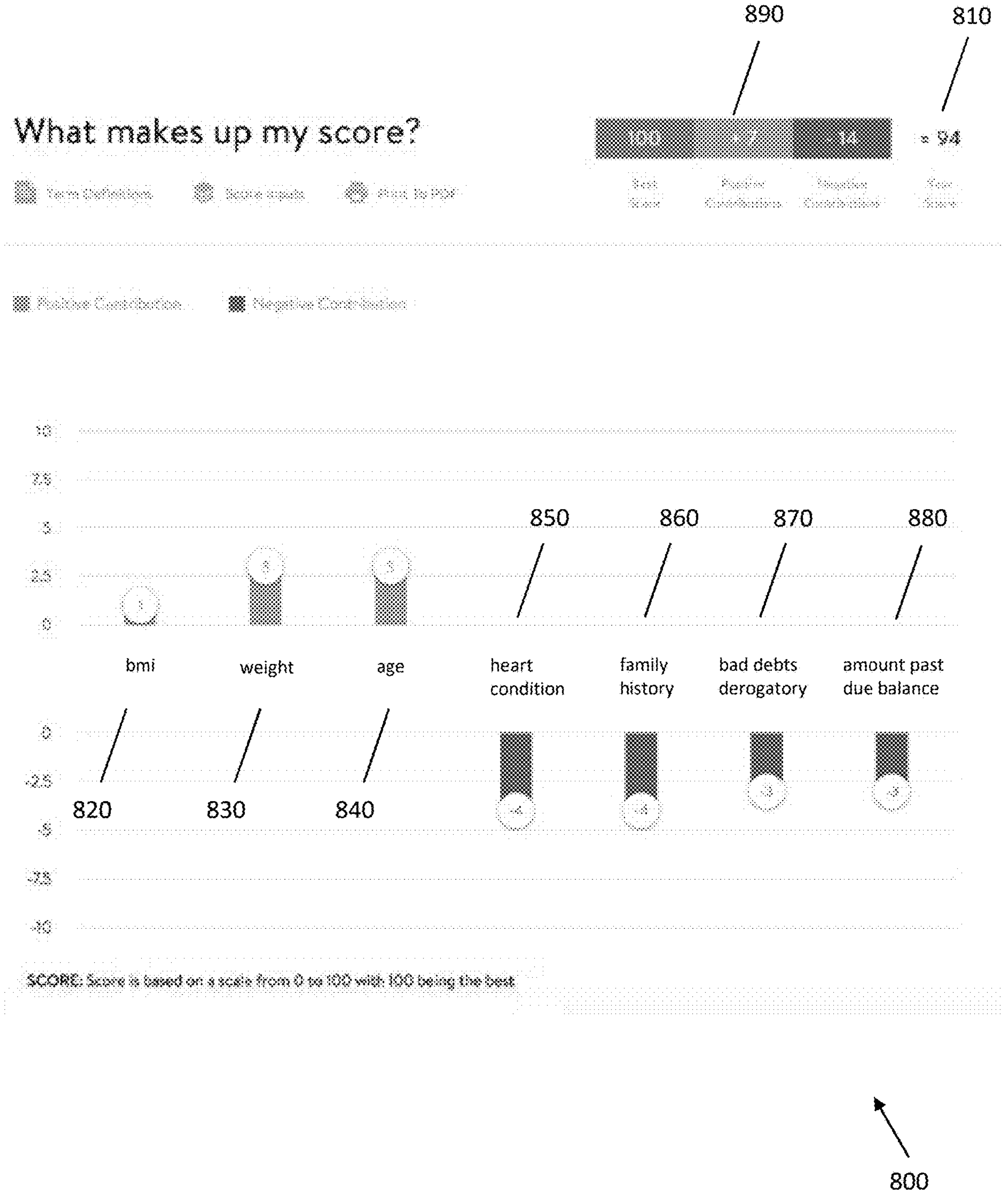
FIG. 8 displays an explanation of a machine learning underwriting model prediction including additive contributions to a risk score, according to an embodiment.
Figure 9:
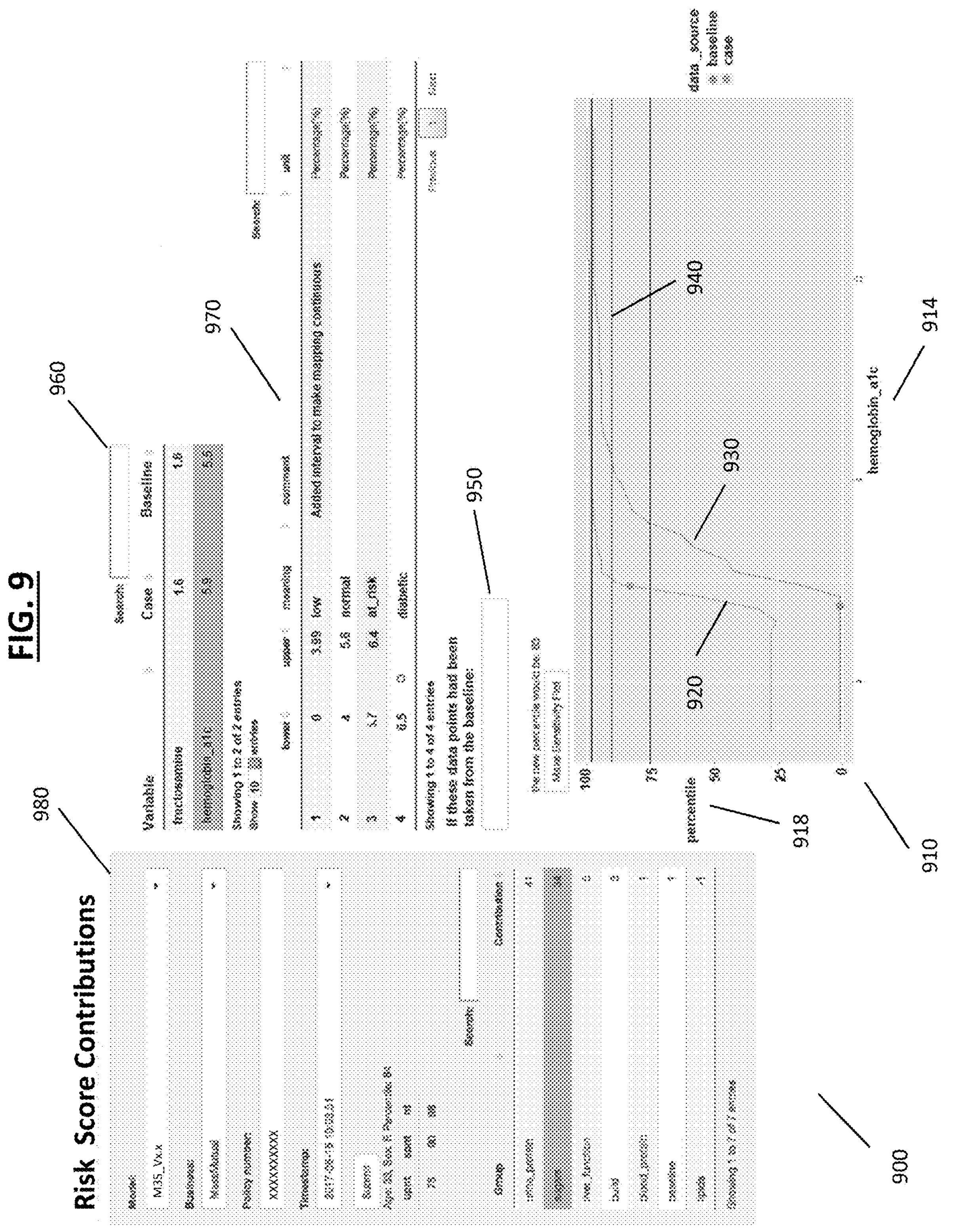
FIG. 9 shows a screen shot of an interactive dashboard of an explanation model for a machine learning underwriting system, according to an embodiment.

Explanations can include either or both text data and graphical data determined by explanation module 250. Example explanation models 250 present additive feature attribution outputs in graphical formats, e.g., as shown in FIGS. 8, 9.

In various embodiments, a rule-based natural language component of explanation methods 250 translates model outcomes 260 into standardized text explanations. Text explanations can describe risk scoring outcomes 264 and underwriting decisions 268. Text explanations can be aimed at interpretability at a holistic level 274 and at a modular level 278. Text explanations can include qualitative information and quantitative information. Examples of modular level text explanations 278 include "A fluidless mortality model assigns risk class X to every male with a BMI this high"; "A fluidless mortality model places a large weight on BMI, and your BMI is Y points higher than average"; "If your BMI were Y points lower, you would have received risk class Z"; "A fluidless smoking propensity model estimated excessive risk of smoking propensity, given that the fluidless application does not require submission of a urine screen and a cotinine test." Examples of holistic level text explanations 274 include "Fluidless applicants are offered the best, lowest-priced risk classes they would have received had they been traditionally underwritten with knowledge of lab results;" "The fluidless application does not qualify as a low risk application, but the applicant can resubmit the application with laboratory tests and biophysical measurements."

In various embodiments, interpretable underwriting system 100 transmits reports of model outcomes 164, such as underwriting decisions, to user devices 180. In various embodiments, interpretable underwriting system 100 also transmits explanations 168 of model outcomes to user device 180. Users associated with a user device 180 may include customers (e.g., applicants for insurance), as well as enterprise users such as insurance agents, underwriters, system developers or other representatives of an insurance company, other financial services company, or insurance broker, among other possibilities. System 100 can generate explanations 168 in real time simultaneously or contemporaneously with generating model outcomes 164. Interpretable underwriting system 100 can report underwriting model outcomes and explanations to user device 180 simultaneously or contemporaneously.

Figure 3:
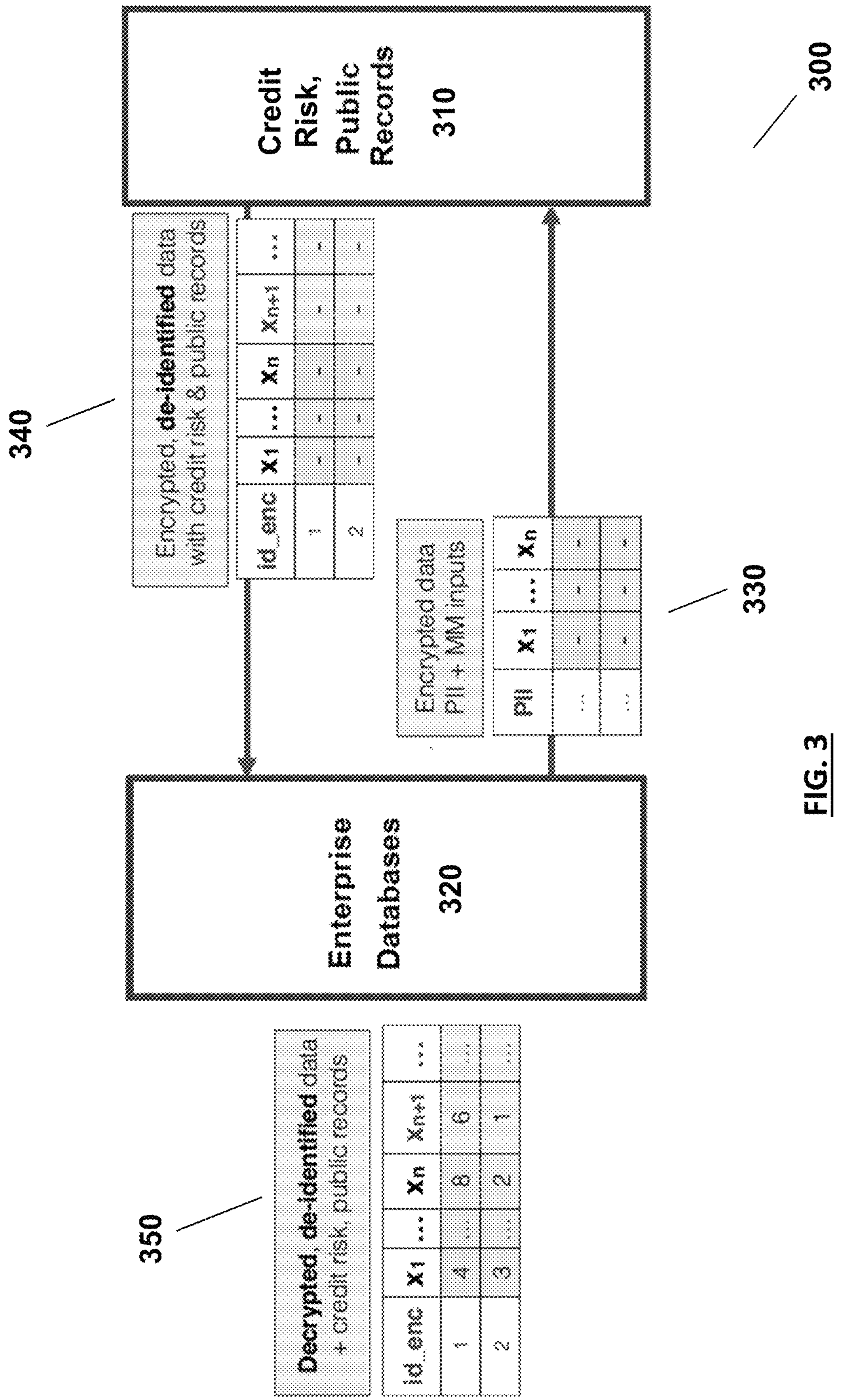
FIG. 3 illustrates a method for appending public records and credit risk data to historical application records, according to an embodiment.

FIG. 3 is a schematic diagram of a data acquisition and transformation procedure used to extract and transform historical applications data for historical insurance applicants of the enterprise, stored in Enterprise Databases 320. The procedure of FIG. 3 was used to acquire appended applications data for the historical applications database 226, and to transform that data via data transformation module 124. Procedure 300 acquired historical applications data and supplemented that data with non-traditional data using techniques that protect privacy rights of the applicants. Appended applications data included non-traditional data attributes that supplement traditional underwriting attributes previously tracked by the enterprise for these historical applicants. A third-party data vendor of Credit Risk/Public Records databases 310 used personally identifiable information to match data 330 to internal records. Subsequently, the third-party database vendor removed the personally identifiable information prior to returning the data set to the sponsoring enterprise at 340 with credit risk and public records attributes appended. At the final stage at 350, the data set in Enterprise Databases 320 was decrypted, and had a de-identified state to protect the privacy of customers.

Figure 4:
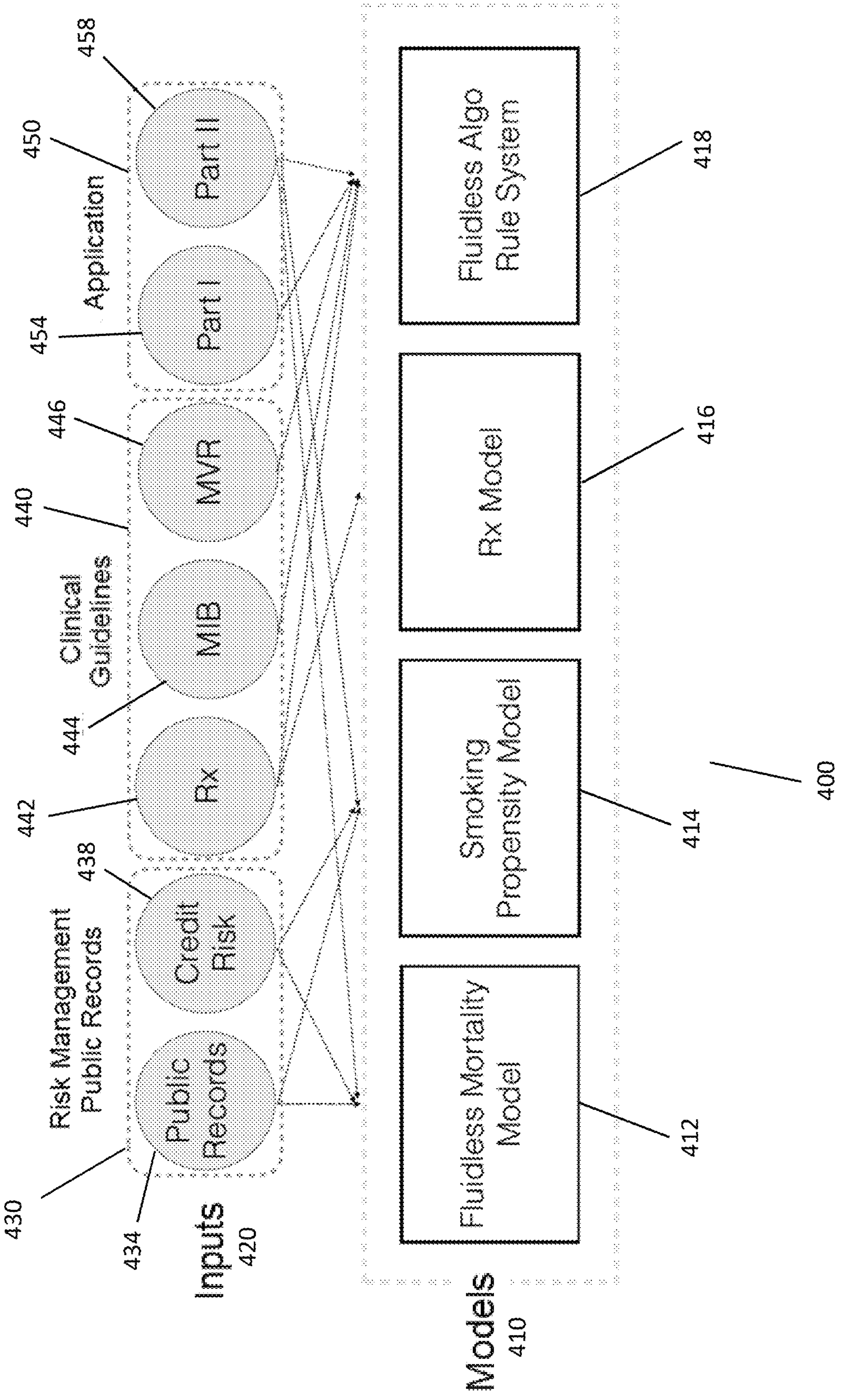
FIG. 4 is a schematic diagram of input data sources and models of a fluidless underwriting method, according to an embodiment.

The fluidless model suite 240 acquires data from four primary data sources in modeling via data acquisition and transformation module 124. FIG. 4 shows a simplified schematic of a system 400 for evaluating program-eligible applicants for approval to receive a fluidless underwriting offer. Data sources of system 400 include two nontraditional underwriting sources, public records 434 and credit risk data 438, and two traditional underwriting sources, client medical interviews ("CMI"; application part II 458), and prescription drug histories (Rx data 442). As used in the present disclosure, the generic term "public data" denotes data relating to applicants of the enterprise obtained from one or more third-party sources, and encompasses both "public records" and "credit risk data."

In various embodiments, "public records" include attributes that pertain to individual-level records that are filed by a public office, such as addresses, education, licenses, property, assets, and financial disclosures. Example public records attributes include the number of lien records on file, time since the most recent bankruptcy filing, number of evictions, and the tax-assessed value of the individual's current address. Public records data set 434 is acquired via third-party API 190. In preparation for model training this data was acquired via the data append procedure 300 of FIG. 3. In production this information is retrieved in real-time through API calls to a third-party vendor of Public Records database 434.

In various embodiments, "credit risk data" include attributes with information that pertains to credit behavior, such as types of open accounts, account balances, derogatory remarks, collections, and bankruptcies. Example credit risk data attributes include the number of collections, ratio of amount past due to amount of total balances, and number of open auto finance accounts. Credit risk data set 438 is acquired via third-party API 190. In preparation for model training this data was acquired via the data append procedure 300 of FIG. 3. In production this information is retrieved in real-time through API calls to a third-party vendor of Credit Risk database 438.

The CMI data set 458 consists of an extensive questionnaire filled out by life insurance applicants. This digital questionnaire covers personal and family health history and behavioral topics. Behavioral topics include motor vehicle violations, smoking, and other topics pertaining to behavioral risks. During model development, non-digital questionnaire responses were digitized, and data transformation procedures were applied to generate features that were incorporated into the model suite 410. In an example, the resulting training data included over 400 columns including both Boolean answers and keyword extraction on open-text fields that align to major medical impairments. In production, digital CMI data 458 and Application Part I data 454 is received via user inputs at user device 180, transmitted via network 170 and stored in fluidless applications database 222. Alternatively, this data is received via paper application and is digitized for storage.

Prescription drug histories data (Rx 442) contains historical prescription drug fills for applicants. An example Rx 442 contains a seven (7) year history per applicant. Each fill record can include the drug generic name, brand name, NDC (National Drug Code), priority, days supply, quantity, prescription fill date, physician name, registration number, and specialty. In an example, the Rx data set constructed during model building contains data for thousands of applicants, including more millions of prescription fill records. In production the Rx data is collected in real-time via API calls to one or more third-party vendors of online computer databases of medical prescription records.

Figure 5:
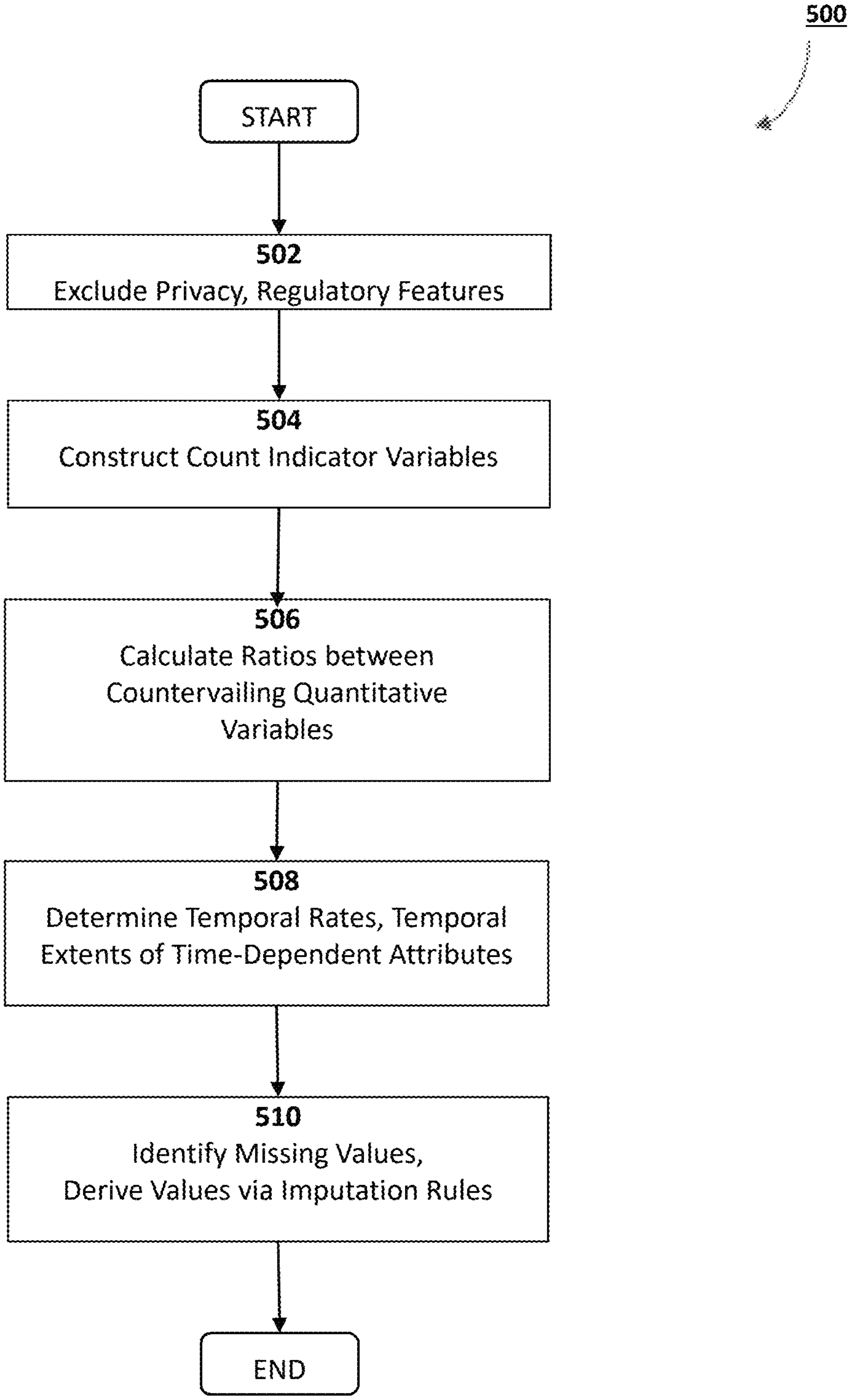
FIG. 5 is a flow chart diagram of data preprocessing procedures of a predictive machine learning module, according to an embodiment.

In the flow chart schematic of FIG. 5, during model development data acquisition and transformation module 124 applied various data pre-processing procedures 500 to acquired data. Step 502 excluded various certain features based on privacy or regulatory considerations and other factors.

Feature engineering procedures 504, 506, and 508 combined or otherwise transformed data attributes in various way to construct engineered variables that were potentially more useful in modeling. For example, in the medical literature, body-mass index (BMI) has been shown to be a more directly causal driver of mortality risk than weight (and especially height) alone. An example of an engineered variable is BMI as a function of height and weight, which addressed the significant interaction between height and weight. In various embodiments, engineered variables also were constructed for credit risk and public records attributes.

Data transformation procedures generated various classes of engineered features: indicators, ratios, and temporal rates. Step 504 constructed count indicator variables. This procedure addressed variables that are measured as a count (e.g., number of felonies) that have a very high proportion of zeros, with a very infrequent but long tail. Feature engineering constructed several indicator variables that reflect any non-zero count of such events.

Step 506 calculated ratios between countervailing quantitative variables. Developing ratios between counts of countervailing quantities can be useful to compute for statistical efficiency. In an example, liens to properties is a weighted ratio of the number of filed or released liens to the number of owned properties (e.g., houses, aircrafts). This ratio was highly predictive in a fluidless mortality model 242 that relied on public records and CMI (application part II 458) as modeling inputs.

Step 508 determined temporal rates and temporal extents of time-dependent attributes. The credit risk and public records attributes often denote counts of quantities within certain temporal extents. As presented, these attributes are overlapping and highly correlated. This procedure develops features that represent rates of change across different durations (kinematics), such as measurements of actual change, velocity, and acceleration. An example of time-dependent attributes include the number of non-derogatory accounts that are provided within the past 3 months, 6 months, 12 months, 24 months, and 60 months. From these attributes, step 508 can compute, for example, the velocity of non-derogatory accounts from 5 years to 2 years ago as the difference between the counts at those time periods divided by the 3-year duration.

Step 510 identified missing values in the acquired data, and derived substitute values for many of the missing values via imputation rules. Missing values were pervasive across the credit risk and public records attributes. In an example of missingness procedure 510, the procedure was designed to avoid adverse impact to any individual score without knowledge of an observed value. In other words, the resulting model score should not be beneficial or detrimental to a given applicant with respect to similar applicants, if an unobserved value is passed as a model input.

In view of these objectives, missingness procedure 510 systematically imputed the median, mode, or a default value conditioned on an applicant's cohort as observed in the training data. A median was imputed if the variable was continuous, a modal value if categorical, and a default setting if specified in provided data dictionaries. During model training, the procedure sampled with replacement from observed values either with a median or modal value depending on variable type. Additionally, for continuous variables, the procedure avoided sampling from the 10% extreme of the tails to avoid over-representing outlying values.

Given an understanding of the acquired data set and of missingness associated with each source, model training of the underwriting models 154, 240 employed univariate analysis 128 of the statistical association between individual attributes and the target outcomes of interest. FIGS. 6A-6D show several examples of this univariate analysis. It should be understood that the charts of FIGS. 6A-6D are disclosed only as illustrative examples of using observations in historical data as a basis for building multivariate models.

Figure 6A:
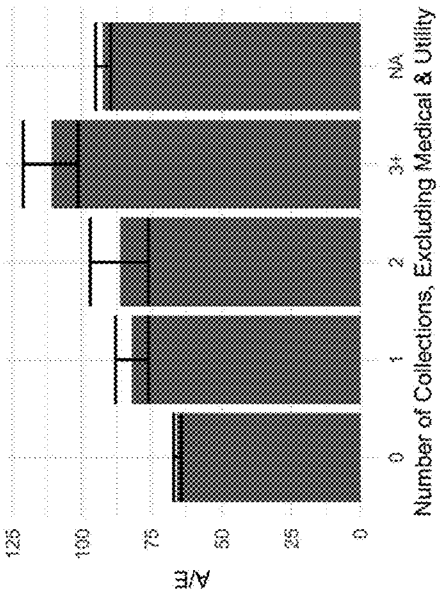
FIG. 6A displays a relationship between an individual's number of collections and input address length of residence, according to an embodiment.
Figure 6B:
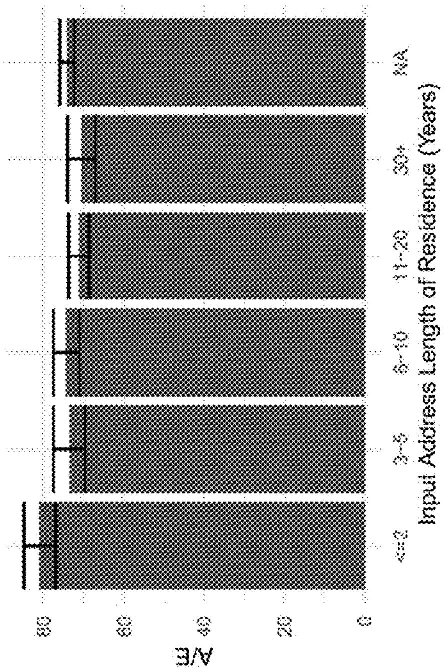
FIG. 6B displays a relationship between an individual's number of collections and input address length of residence, according to an embodiment.

FIG. 6A and FIG. 6B display the relationship between an individual's number of collections (medical and utility excluded) and input address length of residence with survival, as measured by the actual-to-expected (A/E) ratio. The A/E ratio compares the actual number of deaths with the expected number of deaths conditioned on the age, sex, duration of observation, and smoking status makeup of the underlying individuals. A low A/E signifies a low-risk set of individuals, while an A/E of 100% indicates that the expected number of individuals have died. Underwriting protocols aim to stratify a population, here life insurance applicants, to produce pools of risk with target A/E values that drive premiums. In FIG. 6A, number of collections (excluding medical and utility) have a monotonically increasing effect on mortality with 0 collections being associated with an A/E of 65.8% and 3 or more collections with an A/E of 110.9%. In FIG. 6B, input address length of residence has a negative relationship with mortality. A length of residence less than or equal to 2 years is associated with an A/E of 80.9% and a length of residence of more than 30 years has an A/E of 70.4%.

Figure 6C:
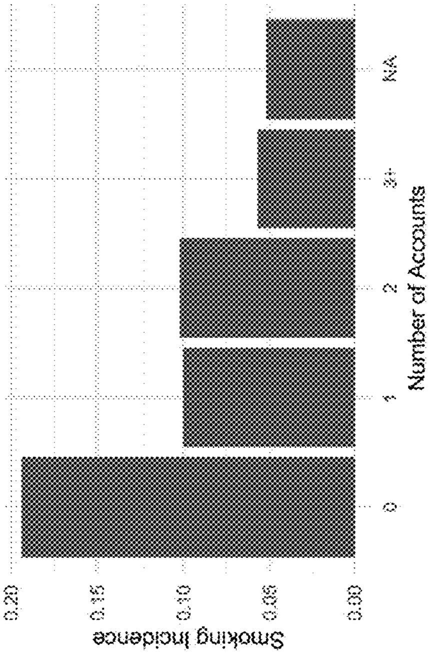
FIG. 6C displays a relationship between an individual's total number of accounts and smoking incidence, according to an embodiment.
Figure 6D:
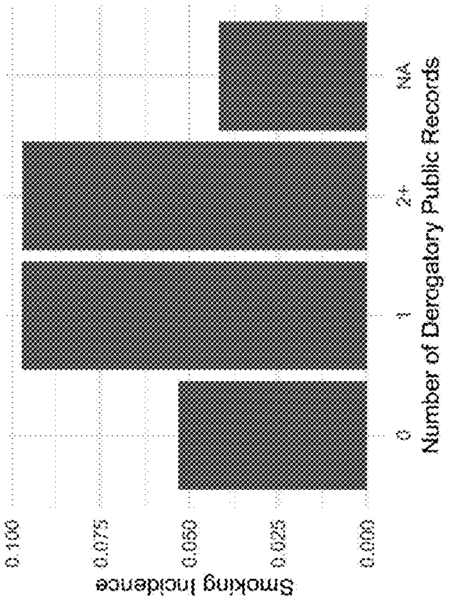
FIG. 6D displays a relationship between an individual's number of derogatory accounts and smoking incidence, according to an embodiment.

FIG. 6C and FIG. 6D show how an individual's number of derogatory public records, which include felonies, liens, bankruptcies, and evictions, and the individual's total number of accounts, are associated with smoking incidence. In FIG. 6C, an individual's total number of accounts has a negative relationship with smoking, with no accounts being associated with smoking incidence of 19.4%, 3.4 times higher than having 3 or more accounts on file, 5.7%. In FIG. 6D, number of derogatory records has a positive relationship with smoking, with one or more derogatory records being associated with 80% higher smoking incidence than having no derogatory records, 9.7% versus 5.3%. In view of significant univariate relationships between these newly acquired data attributes and target outcomes of the present fluidless protocols, an embodiment of the present disclosure builds multivariate models with protective value for mortality and smoking risk.

Initial data acquisition and pre-processing procedures (e.g., data append, missing value imputation, feature generation and exclusion) provide complete data with a sizable, though reduced, set of potential predictors for model construction. The modeling framework is designed to select model inputs from these predictors based on their joint ability to optimize a given objective function of each model in the fluidless model suite 240. This objective is model-specific, e.g., to minimize predicted mortality error or to maximize predicted likelihood of smoking. The Random Forest Modeling module 130 serves as a general, reusable framework that yields relatively parsimonious models while optimizing the specific objective of each model.

Algorithm 1 presents a backward feature selection process that balances held-out performance with rapid, but principled, model development. Beginning with the superset of variables and inclusion of random noise vectors, the algorithm trains a series of models using k-fold cross-validation to generate held-out predictions to compute a model score and an averaged variable importance ranking across all variables. All variables that fall below the importance ranking of random noise are then dropped to produce the set of model covariates for the subsequent iteration. The process is repeated until the covariate list converges, and a final model is trained without the inclusion of the random variables. Corresponding pseudocode of an iterative procedure for selecting a locally minimal set of variables that yields a high-performing model is described as follows:

Algorithm 1: BackwardModelSelection(D, k, HS)

D ← D plus random vectors R = $R_1 \ldots R_j$
iter ← 1
$V_0$ ← Ø
$V_1$ ← attrs (D)
while $V_{iter} \neq V_{iter-1}$ do
model scores S ← Ø
variable importance list Vl ← Ø
for hyperparameter setting hs ϵ HS do
predictions P ← Ø
for f old f in 1 to k do
train model $M_{hs}$ on $D_{1:k\backslash\{f\}}$ with covariate set $V_{iter}$
P ← P ∪ predict ($M_{hs}$, $D_f$)
$Vl_{f,hs}$ ← importance ($M_{hs}$)
$S_{hs}$ ← evaluate (P, D)
M ← $\mathrm{argmin}_{hs}$S
dropped variables DV ← V > R in avg ($Vl_{hs}$)
iter ← iter + 1
$V_{iter}$ ← $V_{iter-1}\backslash$DV
return M In various embodiments, this procedure is applied to construction of both the Fluidless Mortality models 242, 412 and the Smoking Propensity models 244, 414.

In various embodiments, models of the fluidless model suite 240 comprise machine learning models that are trained on various sets of training data. Suitable machine learning model classes include but are not limited to random forests, logistic regression methods, support vector machines, gradient tree boosting methods, nearest neighbor methods, and Bayesian regression methods.

Models of fluidless model suite 240 use one or more models 132, 134, 136 within the Random Forests ensemble 130 for Survival, Regression, and Classification (RF-SRC). Random Forest Modeling module 130 serves as a general, reusable framework that yields relatively parsimonious models while optimizing the specific objective of each model. In Random Forests methods, ensemble learning is improved by injecting randomization into the base learning process. RF-SRC extends Random Forests methods and provides a unified treatment of the methodology for models including right censored survival (single and multiple event competing risk), multivariate regression or classification, and mixed outcome (more than one continuous, discrete, and/or categorical outcome). When one continuous or categorical outcome is present, the model reduces to univariate regression or classification respectively.

Random forests models for classification (model 136) work by fitting an ensemble of decision tree classifiers on sub samples of the data. Each tree only sees a portion of the data, drawing samples of equal size with replacement. Each tree can use only a limited number of features. By averaging the output of classification across the ensemble, the random forests model can limit over-fitting that might otherwise occur in a decision tree model.

In an example, model training used 10-fold cross validation and a grid-search of relevant hyperparameters (number of trees, minimum size of terminal nodes) for random forests.

In various embodiments, the predictive machine learning models identify features that have the most pronounced impact on predicted value. Different types of fluidless underwriting model may identify different features as most important. For example, a model based upon a mortality risk signal may identify different leading features than a model based upon a tobacco propensity signal. In various embodiments, leading model features were extracted from sources such as Public Records data 434, Credit Risk data 438, and CMI data 458.

In an example, the predictive value of model features was measured using the minimal depth of a maximal subtree (7), i.e., shortest distance from the root node to the parent node of the maximal subtree, as a variable importance metric. The importance metric used conventionally for random forests is permutation-based variable importance, a time-consuming procedure. As applied within the global structure of the random forests ensemble, the minimal depth of a maximal subtree is a more efficient importance metric, which is faithful to the global structure of the model and is independent of model task and the values calculated at terminal nodes.

Variable importance metrics for random forests can exhibit biases with respect to the number of chosen splits for features with different distributions and cardinalities. Modeling injected random noise variables to compensate for this effect using a computationally efficient procedure. Injected random noise variables corresponded to several main categories of distributions observed in the data set: (1) normal for continuous values; (2) binary with a proportion set to the mean proportion across all binary variables; and (3) two negative binomial variables for count-based features that exhibit small and large dispersion.

FIG. 4 displays a simplified schematic of a system for evaluating program-eligible applicants for approval to receive a fluidless underwriting offer. System 400 requests inputs 420 from various third-party APIs 430 and 440 and receives fluidless digital applications of the sponsoring enterprise. System 400 tests inputs 410 across a set of fluidless models 410 of the enterprise in order to determine whether to present an accelerated underwriting offer to the applicant. Models 410 include a comprehensive algorithmic rule system 418 and three probabilistic models 412, 414, and 416. In various embodiments, in order to receive approval for presentation of an accelerated underwriting offer, the application must pass all model components 412, 414, 416, and 418. Models 410 can be implemented using a single-processor system including one processor, or a multi-processor system including any number of suitable processors that may be employed to provide for parallel and/or sequential execution of one or more of the model components 412, 414, 416, and 418.

In various embodiments, for one or more of probabilistic model components 412, 414, and 416, the fluidless underwriting protocol determines a quantitative risk score for the fluidless application and determines whether the respective risk score exceeds a set eligibility threshold for the respective model. For each of these model components the system 300 incorporates eligibility thresholds established using a threshold-setting procedure. These eligibility thresholds can be important tools for actuarial analysis, i.e., for determining an observable correlation between policyholder characteristics and cost to the sponsoring enterprise. In an embodiment, the threshold-setting procedure determines a certain percentage of the business of a given risk class assignment to be eligible. The threshold-setting procedure can set cohort-specific thresholds by decreasing volume incrementally until a target mortality impact is reached. The threshold-setting procedure can set different thresholds for the various component models. The threshold-setting procedure can set thresholds within a pre-set range of minimum and maximum risk scores.

Fluidless Algorithmic Rule System 418 stores and applies rules that reflect a comprehensive set of medical and underwriting guidelines developed by experts in underwriting and insurance medicine, but that exclude rules based on clinical laboratory data. In the present disclosure, rules applied by the Fluidless Algorithmic Rule System 418 are sometimes called “non-clinical rules.” In an example, module 418 stores about 4000 non-clinical rules. Each rule determines the best available risk class in the presence of certain values in the application. For example, a high BMI would preclude an applicant from receiving a preferred-risk offer. Fluidless Algorithmic Rule System 418 executes all non-clinical rules across data retrieved from various Clinical Guidelines databases 440. Fluidless Algorithmic Rule System 418 executes all non-clinical rules across data retrieved from Prescription Drug (Rx) database 442, Medical Information Bureau (MIB) database 444 and motor vehicle records (MVR) database 446.

The Prescription Drugs (Rx) input 442 determines whether the application remains eligible in view of publically available information about prescription fills. Additional eligibility criteria are checked via applying the automated rules to other inputs retrieved from MIB database 444 and MVR database 446. Fluidless Algorithmic Rule System 418 can “clear” an algorithmic rule if it identifies adequate cause to override information flagged by the system. If one or more rules of module 418 remain “red,” the system can automatically notify the advisor assigned to the applicant to order a lab test and paramedical examination.

In building the predictive models of the present disclosure, model datasets may have populations in the hundreds of thousands or millions of individuals. In an example Fluidless Mortality Model 412 was built from historical applications of the sponsoring enterprise containing 1.3 MM records. Data preprocessing retained applicants with no missing CMI, BMI, or public records, yielding a training set of around 230,000 historical applications 226. In an example, the Rx data set 442 constructed during model building contained data for more than 120,000 applicants, including more than three million prescription fill records.

Fluidless Mortality Model 412 predicts mortality risk of a given individual relative to the individual’s age and sex cohort without use of clinical data. Fluidless Mortality Model 412 seeks to identify fluidless applicants that pose the lowest mortality risk, to accelerate their experience with a simplified underwriting process. In processing a fluidless application, if Fluidless Mortality Model 412 determines a mortality risk score above a predetermined level, then the system automatically notifies the advisor assigned to the applicant to order a lab test and paramedical examination.

Traditional methods of underwriting for mortality employ survival modeling for predicting ground-truth mortality. Survival modeling seeks to approximate the survival function, which describes the probability that an event, occurring at a random variable time, occurs later than some given time. In lieu of employing survival modeling as is conventional for predicting ground-truth mortality, Fluidless Mortality Model 412 can use a regression framework 134 to predict relative mortality. Regression framework 134 was seen to avoid temporal inconsistencies with public records and credit risk attributes that would occur in using the full range of exposure in survival modeling, and enabled more efficient model development in dealing with hundreds of predictors and iterative feature selection.

Fluidless Mortality Model 412 was trained using a regression framework with historical underwriting risk classes, using assigned risk classes from a retrospective study to generate mortality assumptions in the applications in training data. In order to incorporate nontraditional data sources (public records and credit risk) to measure mortality risk, an initial stage of the modeling pipeline was to ensure that any attribute used as a potential covariate in the model is actuarially justified. Using the data preprocessing steps 500 of FIG. 5, the modeling pipeline fitted a survival model 132 on solely the public records and credit risk attributes 430. The features that showed no predictive signal directly with observed deaths were excluded from subsequent steps of the modeling pipeline using regression.

To assess the performance of each regression model, the Fluidless Mortality Model 412 incorporates a mortality-impact metric that is designed to weigh actual low-risk applicants and predict low-risk applicants more heavily. In various embodiments, the fluidless underwriting protocol is primarily concerned about individuals who receive a low-risk score from Fluidless Mortality Model 412 and are likely to be accelerated underwriting-eligible, or who truly have low relative mortality. To account for this, the mortality-impact metric computes a weight, $w_i$, for each individual i such that a low prediction or true label is associated with a higher weight, causing the error associated with these individuals to have a larger penalty:

$$w_i = \frac{1}{\min(y_i, y_i)}$$

This weight is multiplied by the difference between the prediction and the label, and the total error is taken as the square root of the mean of these weighted differences. In the present disclosure, the resulting mortality-impact metric is denoted as the mortality-impact weighted root mean-squared error (WRMSE):

$$e_w = \sqrt{\frac{\sum_i (y_i - y_i) * w_i}{N}}$$

Smoking Propensity Model 414 addresses a challenge of the fluidless underwriting protocol, that actual knowledge of an individual's tobacco usage is a central factor in assessing mortality risk. Clinical laboratory tests detect nicotine metabolites in fluid samples, but this indicator of tobacco usage is missing in the fluidless underwriting process. Rather than rely solely on self-reporting of tobacco usage, the fluidless modeling suite includes a Smoking Propensity Model 414 that specifically predicts tobacco usage.

Based on tobacco usage of the insured that is self-reported in the digital fluidless application, the accelerated underwriting offer includes the two risk classes UPNT and SPT, which are the best non-tobacco and tobacco fluidless risk classes respectively. If no tobacco usage were disclosed in the fluidless application, the conventional risk assignment would be the standard non-tobacco risk class UPNT, while if tobacco usage were disclosed in the fluidless application, the conventional risk assignment would be the standard tobacco risk class (SPT). In an example, the Smoking Propensity Model 414 identifies tobacco usage by a significant portion of the unreported tobacco users that otherwise would be assigned a UPNT status, and denies these individuals accelerated underwriting. Performance testing has confirmed that the Smoking Propensity Model 414 significantly reduces adverse impacts on mortality risk of the fluidless underwriting program due to unreported tobacco usage.

Smoking Propensity Model 414 can define smoking as a binary outcome. The training data set assigns the status of smoking to individuals who either had a positive nicotine test from urine or saliva or were offered a tobacco risk class. In the training data, males have a smoking status a higher rate than females across all ages. Younger males have a smoking status at a much higher rate than older males. The rate of smoking status has significantly decreased over time during the time period of the historical applications. Based on testing of various modeling methods, random forests performed comparably to, or better than, the other methods. This model class was selected for the Smoking Propensity Model 244, 414 for consistency across the fluidless model suite 240. The smoking propensity model is a classifier (using RF-C model 136) that estimates the propensity for an individual to be a smoker, i.e., for the smoking status of a particular individual to be TRUE given a set of predictors.

In various embodiments, the Smoking Propensity Model was initialized with the same set of attributes as the Fluidless Mortality Model, and was trained in two different model versions. A first smoking propensity model was trained with both credit risk and public records, while a second smoking propensity model was trained with only public records. A version of the smoking propensity model adopted as Smoking Propensity Model can be trained with both credit risk and public records. Feature selection resulted in 59 attributes. A lift curve for the Smoking Propensity Model 414 indicates that this model identifies approximately 2.5 times more smokers in the first decile than the overall baseline smoking rate.

The Rx Model 416 (Prescription Fills model 246) predicts the probability of declining an accelerated underwriting offer or issuing a substandard offer conditioned on information derived from prescription drug fills. Rx records in training data were pulled from a third-party pharmacy database vendor. The Rx data included prescribed drugs and dosages, dates filled and re-filled, therapeutic class, and name and specialty of the prescribing doctor. In addition, Rx data included a priority associated with each drug based on an analysis of each individual's prescription drug history. Priority is indicated by color labeling of red, yellow and green, with red signaling the greatest risk.

Given a set of Rx fills for each individual, model training can generate aggregate features to characterize the full prescription drug history. These features include the overall variety and total fills of drugs (by red, yellow, and green priority), variety and total fills of recent high-risk (red) drugs, variety and total fills of opioid-related drugs, and number of physicians with specialties related to severe diseases. In addition, model training selected the top 50 generic drugs by calculating the proportion of substandards and declines associated with each drug, ranking their importance after adjusting for the joint credibility of all drugs and their interactions using a Markov chain Monte Carlo approximation. The most important drugs are generally prescribed for diabetes, heart disease, mental health, and other serious conditions. The final set of predictors also included age, gender and BMI.

Random forest classifier 136 was selected for Rx Model 416. In other embodiments, Rx Model 416 incorporates a classifier based on a model class other than random forests. If Rx Model 416 indicates an applicant has high risk, then the system automatically notifies the advisor assigned to the applicant to order a lab test and paramedical examination.

Figure 7:
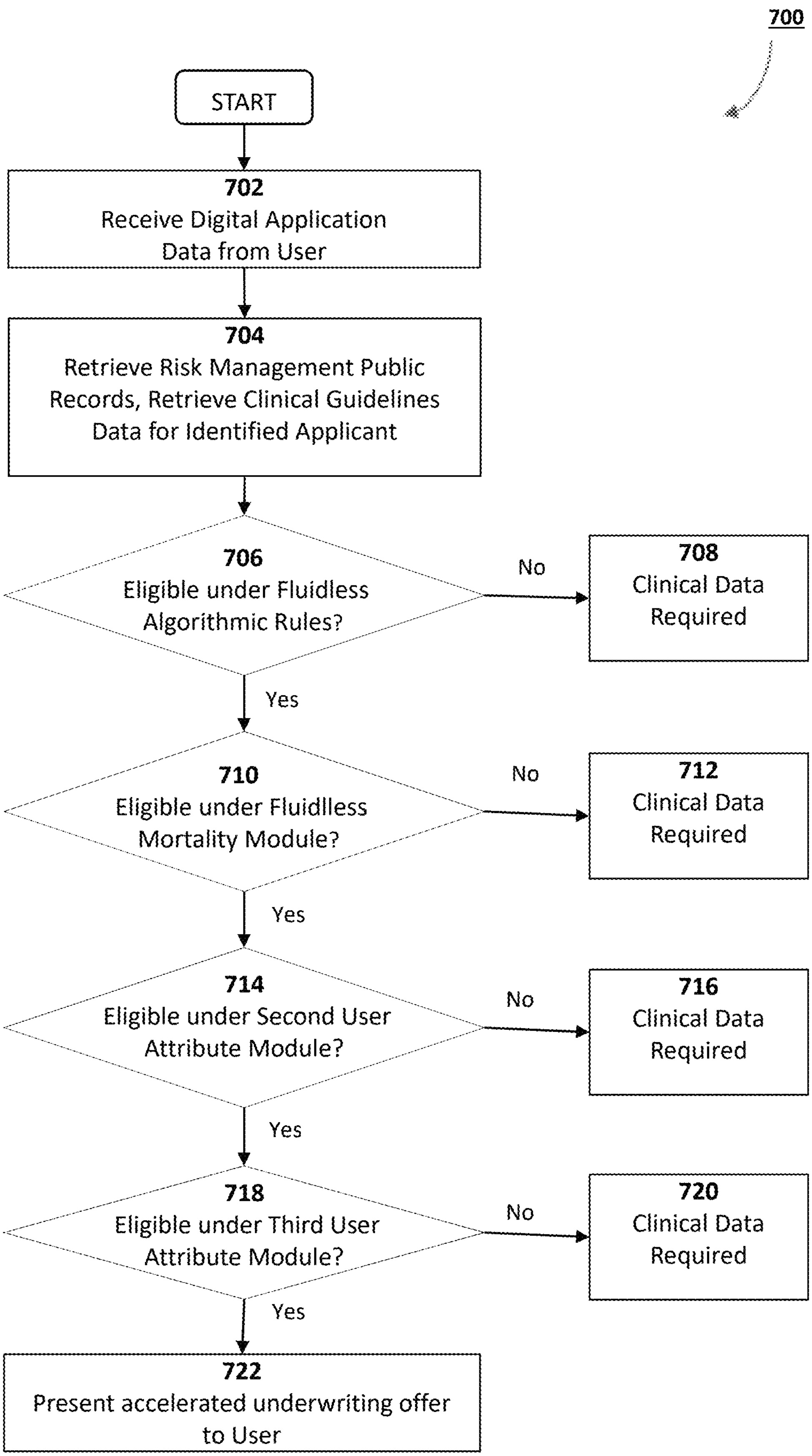
FIG. 7 is a flow chart diagram of a fluidless underwriting protocol, according to an embodiment.

In an example of a method 700 for fluidless underwriting as shown in FIG. 7, at step 702 the fluidless underwriting system receives a fluidless digital application, e.g., from an applicant device. At an initial stage of processing, the analytical engine 114 screens the application for program eligibility based on a set of program parameters. Program eligibility parameters include (a) an age of the insured between 17 and 59, inclusive; (b) BMI between 18-31; (c) a maximum face amount of the insurance policy; (d) the requested life insurance product is included on a list of available products.

In an optional embodiment of step 702, if initial screening determines that an applicant meets the program parameters, to proceed with fluidless underwriting an advisor representing the sponsoring enterprise must also select the option for fluidless consideration during application submission. Advisors experienced with the criteria for eligibility for accelerated underwriting (also herein called "accelerated underwriting program"), can review the submitted digital application and may identify applicants that are unlikely to qualify for fluidless underwriting (e.g., if the applicant is diabetic or overweight) so as not to delay ordering clinical data.

If the application meets initial eligibility requirements, the method then retrieves 704 public records and clinical guidelines for the identified applicant. The application must pass a set of risk-related criteria to receive a fluidless offer. At step 706, the method determines eligibility of the fluidless application under Fluidless Algorithmic Rules. If the fluidless application is eligible under the Fluidless Algorithmic Rules, the process proceeds to step 710. If the fluidless application is not eligible under the Fluidless Algorithm Rules, e.g., because one or more critical algorithmic rules result in a "red" determination, the process declines 708 the accelerated underwriting offer. In an example, Fluidless Algorithm Rules result in a "red" determination if any major medical risk or non-medical risk (lifestyle risk) appears on the fluidless application. In various embodiments, the process declines the accelerated underwriting offer by automatically notifying the user (applicant) via user device 180 that it is necessary to obtain a lab test and paramedical examination and/or by automatically notifying an advisor assigned to the application to order the lab test and paramedical examination. In various embodiments, the process generates and displays an explanation for display to the user when notifying the user of the declined application.

At step 710, the method determines eligibility of the fluidless application under the Fluidless Mortality Module. If the fluidless application is found eligible by the Fluidless Mortality Module, the process proceeds to step 714. If the fluidless application is not found eligible by the Fluidless Mortality Module, e.g., because the applicant is determined to have an unacceptable mortality risk score, the process declines 712 the accelerated underwriting offer, e.g., by automatically notifying the user (applicant) that it is necessary to obtain a lab test and/or by automatically notifying an advisor assigned to the application to order the lab test and paramedical examination.

At step 710, the method determines eligibility of the fluidless application under the Fluidless Mortality Model by determining a mortality risk rank. As used in the present disclosure, a mortality rank can include a raw mortality score. In another embodiment, a mortality risk rank incudes a tier or group corresponding to a given mortality score, wherein the tier or group is selected from a "high risk" and "low risk" tiers or groups that are based upon a distribution of mortality risk scores for a population of new business applicants of the enterprise. A mortality risk rank can include a percentile classification of a given mortality risk score relative to all mortality risk scores for a population of customers of the enterprise. A mortality risk rank can include a combination of the above types of rank. Similarly, in the present disclosure other risk ranks such as "second risk rank" and "third risk rank" may include one or more of these embodiments.

At step 714, the method determines eligibility of the fluidless application under the Second User Attribute Module. The Second User Risk Attribute model predicts likelihood of at least one risk factor that normally can be indicated by clinical data when included in an application. The Second User Attribute Model can be a Smoking Propensity Module. The Smoking Propensity Module predicts whether the applicant is a smoker or non-smoker, which normally can be indicated in clinical data included in typical medical examinations that screen for nicotine and cotinine in the urinalysis. If the fluidless application is found eligible by the Second User Attribute Module, the process proceeds to step 718. If the fluidless application is not found eligible by the Second User Attribute Module, e.g., because the applicant receives a smoking binary classification by the Smoking Propensity Module, the process declines 716 the accelerated underwriting offer, e.g., by automatically notifying the user (applicant) that it is necessary to obtain a lab test and/or by automatically notifying an advisor assigned to the application to order the lab test and paramedical examination.

At step 718, the method determines eligibility of the fluidless application under the Third User Attribute Module. The Third User Risk Attribute Module predicts likelihood of at least one additional risk factor that normally can be indicated by clinical data when included in an application, wherein the additional risk factor is different from the risk factor predicted by the Second User Risk Attribute Module. The Third User Attribute Model can be a Prescription Fills (Rx) Module. Prescription Fills (Rx) Module can predict whether the applicant has or is at risk from various diseases and conditions that normally can be indicated in clinical data. If the fluidless application is found eligible by the Third User Attribute Module, the process proceeds to step 722. If the fluidless application is not found eligible by the Third User Attribute Module, e.g., because the applicant receives a substandard or decline classification by the Prescription Fills (Rx) Module, the process declines 720 the accelerated underwriting offer, e.g., by automatically notifying the user (applicant) that it is necessary to obtain a lab test and/or by automatically notifying an advisor assigned to the application to order the lab test and paramedical examination.

In various embodiments, in the event of any of decline steps 708, 712, 718, and 720, the method generates and displays to the user an explanation file including the adverse model outcome. The explanation file may include a modular explanation 278 of the particular fluidless model component that generated the decline decision (failure to meet eligibility requirements for the relevant model component). The explanation file may include a holistic explanation 274 of the fluidless predictive model, e.g., required eligibility determinations by three component models; and may include an explanation of the decision to decline expedited underwriting.

In determining eligibility of the fluidless application against multiple risk attributes, in general the order of eligibility determinations is not critical. The operations can be performed in parallel or concurrently, and the order of the operations may be re-arranged. In the method 700, the steps of determining eligibility under Fluidless Algorithmic Rules 706, determining eligibility under Fluidless Mortality Module 710, determining eligibility under Second User Attribute Module 714, and determining eligibility under Third User Attribute Module 718 may be carried out in any order or concurrently.

At step 722, having passed all criteria 706, 710, 714, and 718, the method automatically presents an accelerated underwriting offer in the fluidless digital application. In various embodiments, step 722 automatically communicates the accelerated underwriting offer to the user (applicant) via user device 180 and/or automatically notifies an advisor assigned to the application to communicate the accelerated underwriting offer to the applicant.

In various embodiments, the system and method of the present disclosure use additive feature attribution techniques to approximate the outputs of survival mortality models in "interpretable" outputs. Additive feature attribution is a technique used to approximate the output of a complicated multivariate function as a linear one on a binary feature space. By building a model in this binary space, the linear coefficients represent the effect of the "presence" or "absence" of a feature on the model's output. For instance, in natural language processing applications, this binary feature is often defined to be the presence or absence of a word.

In the general case, given a data instance $x=\{x_1, x_2, \ldots, x_d\}$ and a model f, this technique employs an interpretable function $h_x:\{0,1\}^d \rightarrow \mathbb{R}^d$ that maps a binary vector to the original feature space via the formula $h_x(\{1, 1, \ldots 1\})=x$. A common choice for $h_x$ is to define this invertible function so that $$h_x^{-1}(x')_i = 1$$

$(x')_i=1$ when $$x_i' = x_i \text{ and } h_x^{-1}(x')_i = 0$$

otherwise. In this way, given a new data instance x', the ith "interpretable feature"

$$z_i' = h_x^{-1}(x')_i$$

can be considered the Boolean answer to the question "Is $$x_i'$$

equal to $x_i$"?

An additive explanation model $$g:\{0,1\}^d \to \mathbb{R},\ g(z) = \phi_0 + \sum\nolimits_{i=1}^{d} \phi_i z_i$$

attempts to approximate $$g\left(h_x^{-1}(x')\right) \approx f(x)$$

when $x' \approx x$. As a result, an effect $\phi_i$ is attributed to each feature $x_i$, and summing the effects of all feature attributions approximates the output on x:

$$f(x) \approx g\left(h_x^{-1}(x)\right) = g(\{1, 1, \ldots 1\}) = \phi_0 + \sum\nolimits_{i=1}^{d} \phi_1$$

The system and method of the present disclosure can employ the additive feature attribution methodology of LIME (Local Interpretable Model-agnostic Explanations), an explanation technique that explains the predictions of any classifier, of Marco Tulio Ribeiro, Sameer Singh, and Carlos Guestrin, "Why Should I Trust You?: Explaining the Predictions of Any Classifier," KDD '16 Proceedings of the 22nd ACM SIGKDD International Conference on Knowledge Discovery and Data Mining Pages 1135-1144, Aug. 13-17, 2016.

In various embodiments, the system and method of the present disclosure employ SHAP values, a feature attribution method that draws on game theory. Scott M. Lundberg, Su-In Lee, "A unified approach to interpreting model predictions," NIPS'17 Proceedings of the 31st International Conference on Neural Information Processing Systems, Pages 4768-4777; Dec. 4-9, 2017. SHAP values (SHapley Additive exPlanation) is based on Shapley values, a technique used in game theory to determine how much each player in a collaborative game has contributed to its success. Given a cooperative game in which different sets S of players can collaborate and produce certain outcomes V(S), Shapley values provide a method to divide the value generated by the coalition among the different players. The SHAP value framework extends this solution to the problem of dividing the model outcome f(x) between different interpretable features.

In SHAP values, the marginal contribution of a certain feature represents how much the "presence" of that feature changes the outcome of the function, given the "presence" of certain other features. In an example, S represented a subset of the features {1, 2, . . . d} and $z_S$ represented the binary vector where $z_i=1$ for $i \in S$. The marginal contribution $$\phi_j^S$$

for $j \in S$ was defined as the difference in f when the jth feature in $z$ is switched to a 1:

$$\phi_j^S = f(h_x(z_{S \cup j})) - f(h_x(z_S))$$

The SHAP value for a certain feature was then defined as a weighted average of all of its marginal contributions:

$$\phi_i = \sum\nolimits_S \frac{|S|!(d-|S|-1)!}{d!} \phi_i^S$$

This weight represents the number of times the set S can appear as the first |S| features in the set of all possible orderings of the features.

As a method for generating intuitive explanations of survival mortality model outputs, SHAP values feature attribution offers the advantage of satisfying three desirable properties for interpretability. First, this technique exactly approximates the function it is explaining:

$$f(x) = g\left(h_x^{-1}(x)\right).$$

(x)). Second, if a variable $x_i$ is missing or unknown, its contribution $\emptyset_i$ is 0. Third, for two models f and f', if $$\phi_i^S(f) \ge \phi_i^S(f')$$

(f') for all subsets S, then $\emptyset_i$(f) is greater for f than for f'.

In various embodiments, the choice of how to compute or estimate $f(h_x(z_S))$ depends on what assumptions are made. This technique yields the expected model output on a data point when only the features in S are known:

$$f(h_x(z_s)) = E[f(x_{-S} \mid x_S)]$$

The additive feature attribution technique assumes feature independence and model linearity, as in the Kernel SHAP method described by Lundberg and Lee. This embodiment can approximate this expected value as $f([x_S, E[x_{-S}])$ by swapping in expected values—or any other reference value—for the unknown input features.

Lundberg and Lee show that the sums which define each SHAP value are the solution to a constrained weighted linear regression problem on samples $z\varepsilon\ \{0,1\}^d$ and labels $f(h_x(z))$, and this characteristic allows computation time to be reduced significantly with a sampling approximation.

In mapping from the interpretable space to the original data space, $h_x(z)$ is defined so that for features i for which $z_i=0$, the corresponding data point $x_i$ is imputed to be a median value or mode for an age-sex cohort. In the present disclosure, these imputations are sometimes called "baseline" values. Baseline values are also used to handle missing data in production versions of additive feature attribution for the predictive machine learning mortality models.

In various embodiments, groupings of variables are used to aggregate the signal from a family of variables into a single "interpretable feature." This feature aggregation can make the explanations more intuitive, and can reduce the dimensionality of the interpretable feature space so that fewer samples are needed for the regression step. Feature groups can be hard-coded into model objects for the fluidless suite of underwriting models.

In an example, the machine learning predictive mortality modeling systems methods of the present disclosure employed the R SHAP package in implementations of SHAP values feature attribution. Correctness tests showed that a sampling-based algorithm implemented by Lundberg and Lee in the Python object-oriented programming language, https://www.python.org, correctly recovered SHAP values in the simple case of linear regression predictive modeling.

In various embodiments, two algorithms for calculating SHAP values were implemented in Python: a sampling-based algorithm called "Kernel SHAP," and a specialized algorithm called "Tree SHAP" that only works for tree-based models. The "Tree SHAP" algorithm can utilize structure from the model itself to better approximate $E[f(x_{S}|x_S)]$ when feature independence is violated. Scott M. Lundberg, Gabriel G. Erion, Su-In Lee, "Consistent Individualized Feature Attribution for Tree Ensembles"; http://arxiv.org/abs/1802.03888 (2018). Comparing the results of the two algorithms on an XGBoost Cox survival trained with NHANES data provided with the SHAP package showed that if the data is appropriately summarized in clusters used for the baseline input values, the L2 norm of the difference in the explanations from the two methods tends to shrink.

In an example, a demo algorithm for calculating interpretability data based on SHAP values was implemented in R. Corresponding pseudocode is described as follows.

```
library(ISLR)
library(dplyr)
library(SHAP)
library(randomForest)
dat←Auto %>%
mutate(origin=as.factor(origin),
name=as.character(name)) %>%
group_by(name) %>%
sample_n(1) %>%
ungroup( )
```

```
glimpse(dat)
#> Observations: 301
#> Variables: 9
#> $ mpg            <dbl> 13.0, 15.0, 17.0, 24.3, 18.1, 20.2, 21.0, 18.0, 1 . . .
#> $ cylinders      <dbl> 8, 8, 8, 4, 6, 6, 6, 6, 6, 6, 8, 6, 6, 8, 4, 4, 4 . . .
#> $ displacement   <dbl> 360, 390, 304, 151, 258, 232, 199, 199, 258, 232 . . .
#> $ horsepower     <dbl> 175, 190, 150, 90, 120, 90, 90, 97, 110, 100, 150 . . .
#> $ weight         <dbl> 3821, 3850, 3672, 3003, 3410, 3265, 2648, 2774, 2 . . .
#> $ acceleration   <dbl> 11.0, 8.5, 11.5, 20.1, 15.1, 18.2, 15.0, 15.5, 13 . . .
#> $ year           <dbl> 73, 70, 72, 80, 78, 79, 70, 70, 71, 71, 74, 75, 7 . . .
#> $ origin         <fct> 1, 1, 1, 1, 1, 1, 1, 1, 1, 1, 1, 1, 1, 1, 1, 2, 2 . . .
#> $ name           <chr> "amc ambassador brougham", "amc ambassador dpl", . . .
```

The demo algorithm was designed to generate an explanation of a random forest model for predicting mpg from other variables relating to an automobile, other than the automobile name:

```
#Set train ids and train model
train_ids←sample(1:nrow(dat), size=floor(nrow(dat)*0.75))
train_dat←dat %>% slice(train_ids) %>% select(-name)
mdl←randomForest(mpg ~., data=train_dat)
```

The algorithm defines a single-argument function that returns model predictions on an input dataframe:

```
predict_fn←function(x) predict(mdl, x)
```

The last part of the algorithm for obtaining an explanation sets "baseline" values for each input variable. This was done by applying the function summarize_mean_or_mode to the training data, creating a data instance in which each variable takes the mean value (if numeric) or mode. The model's prediction referred to this data as the "baseline" contribution:

```
base←summarize_mean_or_mode(train_dat %>% select(-mpg))
```

```
head(base)
#> # A tibble: 1 x 7
#> cylinders displacement horsepower weight acceleration year origin
#> <dbl> <dbl> <dbl> <dbl> <dbl> <dbl> <fct>
#> 15.52 196. 106. 3000. 15.5 76.2 1
predict_fn(base)
#> 1
#> 19.95633
```

The interpretability model was applied to a test case. By default, the columns of the baseline case were used as candidate features to which contributions are assigned. The contribution values add up to the prediction output in a new row:

```
test_case<-dat %>% slice (-train ids) %>% sample_n(1)
```

```
head (test_case)
#> # A tibble: 1 x 9
#>      mpg cylindersdisplacement horsepower weight acceleration year
         origin
#>      <dbl>   <dbl>   <dbl>   <dbl>   <dbl> <dbl> <dbl> <fct>
#> 1    25.5      4 140    89      2755   15.8    77      1
#>      with 1 more variable: name <chr>
predict_fn(test_case)
#>      1
#> 24.15757
shap_explain (predict_fn, test_case, base) %>% round(3)
#>      baseline   cylindersdisplacementhorsepower     weight
#>      19.956       1.368       1.233            0.653      0.760
#>      acceleration               year             origin
#>      -0.057     0.245     0.000
```

In order to obtain explanations for a large number of rows, the algorithm incorporated the function get_all_explanations:

```
        test dat <- dat %>% slice (-train_ids) %>% select (-mpg)
        get_all_explanations(predict_fn, head(test_dat), background_data = base)
#>      baselinecylindersdisplacement      horsepower               weight
#> 1    19.956332.018393e-160.011713330.22220611              0.62843117
#> 2    19.95633 -4.194062e-170.257278900.03605746         -0.08357722
#> 3    19.95633 -5.291520e-01-0.21168287-1.91647893        -2.85656662
#> 4    19.95633 -4.210254e-01-0.20604466-1.83928309        -1.46217009
#> 5    19.956331.212861e+000.97064398-0.01758733            1.87504649
#> 6    19.956332.097031e-170.24408750-0.05172722          -0.04993737
#>      acceleration year          origin
#> 1    -3.405220e-17 -0.25341210.000000
#> 2    4.250448e-01 -0.25545790.000000
#> 3    -4.399291e-17 -0.26054240.000000
#> 4    7.004933e-01 -0.13358910.000000
#> 5    8.289111e-010.2805527 -0.475709
#> 6    1.635000e-024.17547270.000000
```

In the event the inputs do not include a baseline set of values, get_all_explanations will summarize a dataframe passed into the algorithm:

get_all_explanations(predict_fn, head(test_dat), id='name')

```
#>      name                        baseline    cylindersdisplacement    horsepower
#> 1    amc hornet                    20.09987     0.1981247     -0.4915910    0.7400795
#> 2    amc hornet sportabout (sw) 20.09987 -0.22775880.16572270.4313756
#> 3    amc matador (sw)         20.09987-0.6973803 -0.3118325        -1.3014103
#> 4    amc rebel sst               20.09987 -0.4808245 -0.6582439        -1.3659646
#> 5    bmw 320i                  20.09987 1.1350284 0.7338807               0.4993306
#> 6    buick century limited    20.09987 0.1116811 -0.4522107             0.6654143
#>      weight     acceleration          year           origin
#> 1    1.2915819          -0.45426663     -0.8025443         -0.015980223
#> 2    0.4208821          -0.21190377     -0.6799022          0.337395716
#> 3    -2.8478405        -0.37542917     -0.7677830          0.383718225
#> 4    -0.7021966          0.56034122     -0.9264443          0.068179180
#> 5    2.0835170            0.74026148     -0.3831884         -0.277645095
#> 6    0.3303416          -0.03553958      3.5776157          -0.006591287
```

In some applications, it can be desirable to pass in different baseline cases for each row. For example, in an underwriting model that evaluates mortality risk with respect to an age-sex cohort, the baseline should be age-sex cohort specific. In this event, passing in a function that takes in a row will return an appropriate baseline case.

Disclosed embodiments apply additive feature attribution to interpretability of a mortality score and to outcomes of fluidless underwriting. In an example, the mortality score model outputs a quantitative score based on the scale from 0 to 100. The quantitative score 100 represents the lowest risk (healthiest) and the quantitative score 0 represents the most risky.

In order to facilitate analysis of the percentile risk score as an additive quantity, the method and system of the disclosure can set respective thresholds for different risk classes on this scale.

FIG. 8 illustrates an explanation 800 of a machine learning underwriting model prediction including a quantitative score, showing additive contributions to the quantitative score. These additive contributions quantify contributions of a set of fluidless underwriting features to the quantitative score. The quantitative score is a risk score 810 based on the scale from 0 to 100, where 100 represents the lowest risk (healthiest) and 0 represents the most risky. An additive feature attribution explanation model assigned each fluidless underwriting feature an importance value for this particular prediction. The diagram 800 represents additive contributions via vertical bars of respective lengths corresponding to the size of each contribution, in which upward bars have a positive value and downward bars have a negative value. Explanation 800 shows features 820, 830, and 840 that made positive contributions to the risk score 810, and features 850, 860, 870, and 880 that made negative contributions to the risk score 810. Summing 890 the effects of all feature attributions approximates the quantitative score output 810 of the fluidless underwriting predictive model.

As depicted, the analytical engine server (e.g., via the explanation model) may generate a report to be displayed for the user (e.g., end user and/or an administrator), such as the explanation 800. The explanation 800 may include an overall risk score 810, which is calculated based on positive and negative contributions (e.g., additive contributions). To further describe the risk score 810, the explanation 800 also displays categories that have positively or negatively impacted risk score 810 (e.g., features 820-880). Each feature may correspond to an additive contribution that is used to calculate the risk score 810. Thereby, viewing the features 820-880 allows the end user to understand and interpret the risk score 810.

Each feature may also include a graphical indicator corresponding to the magnitude of each respective feature and its impact on the score 810. For instance, the features depicted in FIG. 8 may have a corresponding vertical bar where the length of each bar represents the magnitude of each feature. In contrast, the direction of each vertical bar represents whether each feature has impacted the score 810 in a negative or positive way. Each feature may also include a numerical score. Using the graphical elements depicted in FIG. 8, the end user can easily interpret important factors that have caused the analytical engine server to calculate the risk score 810.

For instance, feature 830 graphically describes that the end user's weight has positively impacted his/her risk score. The height of the vertical bar for the feature 830 illustrates that the end user's weight has a more significant impact on the end user's score than his/her BMI. In contrast, feature 860 illustrates that the end user's bad debt has negatively impacted the user's risk score.

In some embodiments, the analytical engine server may allow the user to simulate future scores by adjusting one or more additive contributions depicted in the explanation 800. For instance, the features 820-880 may include an adjustable/interactive graphical element where the user can revise the scores to identify how the overall score would be impacted. For instance, the end user may change the score for past due balance (i.e., feature 880) by interacting with the feature 880 (e.g., interacting with the vertical bar and adjusting its height or direction). The analytical engine server may then dynamically execute various protocols described herein to recalculate the user's risk score and dynamically revise the explanation 800.

A model interpretability tool incorporated the interactive dashboard 900 shown in the screen shot of FIG. 9. This tool was used to explore contribution values of test cases passed through the fluidless model suite. For a given policy number and a mortality risk model, the tool displayed the SHAP values for each group and other information about the case's data.

The model interpretability tool 900 gives users a way to explore conditional signals that are aggregated into the SHAP value. Once an interpretable feature is selected, a user has the option to explore the marginal contributions O that make up the SHAP value. Users can thereby explore how that group interacts with other variables. Using a form 950 "If these features had been taken from the baseline," a user can choose a subset of interpretable feature group S and see how this choice affects the output $f(h_x(z_{-S}))$. The formula specifies –S to represent the interpretable features not taken from the baseline.

Using variable selection window 960, users can select an original feature i and optionally a subset S. Based on the selected features, the tool generates a plot 910 of value of Hemoglobin A1C 914 against Percentile 918. Plot 910 shows how $f(h_x(z_{-S}))$ changes as $x_i$ changes. This function provides a way to define the marginal contribution $f(h_x(z_{S \cup i}))-f(h_x(z_{-S}))$. The plot 910 also shows how $f(h_x(z_0))$ changes as $x_i$ changes, thereby depicting the marginal contribution of feature i on the baseline or "null" case.

The dashboard screenshot of FIG. 9 displays a case in which the mortality model penalizes an individual for a value of Hemoglobin A1C known to be an unhealthy range. (Although this example displays a plot for a clinical risk factor, the same procedures apply to display of contribution values of non-clinical risk factors). In plot 910, upper line 920 ("case") shows how the individual's percentile changes with this variable. The line 920 shows that had the value been lower and everything else been the same, the person could have been below the threshold level 940 required for the best risk class. Lower line 930 ("baseline") shows percentile changes of a baseline person with this variable.

Table 970 shows upper and lower thresholds and meanings ("low," "normal," "at risk," and "diabetic") assigned by the mortality model to various value ranges of the variable Hemoglobin A1C. A dashboard panel 980 shows related information on mortality model contributions, e.g., that 34 of the individual's 84 percentile points are attributed, overall, to the sugar values shown at the top.

Users such as model developers can employ the explanation tool 900 to identify inconsistencies and undesirable behavior in machine learning underwriting algorithms. In an example, the tool 900 helped users visualize that prototype fluidless machine learning underwriting algorithms were applying unfavorable imputation rules to certain missing non-clinical variables.

While various aspects and embodiments have been disclosed, other aspects and embodiments are contemplated. The various aspects and embodiments disclosed are for purposes of illustration and are not intended to be limiting, with the true scope and spirit being indicated by the following claims.

The foregoing method descriptions and the interface configuration are provided merely as illustrative examples and are not intended to require, or imply, that the steps of the various embodiments must be performed in the order presented. As will be appreciated by one of skill in the art, the steps in the foregoing embodiments may be performed in any order. Words such as "then," "next," etc., are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc., may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code, with it being understood that software and control hardware can be designed to implement the systems and methods based on the description here.

When implemented in software, the functions may be stored as one or more instructions or codes on a non-transitory computer-readable or processor-readable storage medium. The steps of a method or algorithm disclosed here may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

What is claimed is:

1. A method for processing an electronic application, comprising:

receiving, by a processor, a plurality of variables of the electronic application, the plurality of variables for the electronic application excluding clinical data for an applicant;

retrieving, by the processor, public data identified with the applicant of the electronic application;

executing, by the processor using the plurality of variables, a first predictive machine learning model by inputting selected features from the plurality of variables for the electronic application and the public data identified with the applicant of the electronic application to predict a mortality risk for the electronic application, wherein the first predictive machine learning model is trained by inputting a plurality of historical application records, wherein training the first predictive machine learning model comprises:

generating a set of model variables based on the plurality of historical application records;

iteratively training one or more models using the set of model variables and removing, in at least one subsequent iteration, at least a portion of the set of model variables based on a variable importance ranking for the set of model variables until the set of model variables converges; and training the first predictive machine learning model using the converged set of model variables;

executing, by the processor using the plurality of variables, a second predictive machine learning model to predict a propensity of the applicant of the electronic application to be a smoker;

determining, by the processor using predictions generated by the first predictive model and the second predictive model, a risk group for the electronic application;

executing, by the processor, an explanation model configured to generate an explanation file for display on a user interface, the explanation file including interpretability data based on determination of the risk group; and generating, by the processor, explanation data derived from the explanation file for display on a user interface, the explanation file including interpretability data based on determination of the risk group.

2. The method of claim 1, further comprising:

executing, by the processor using the plurality of variables, a third predictive model to predict a disqualifying medical risk associated with the electronic application, wherein the risk group further corresponds to the disqualifying medical risk.

3. The method of claim 2, wherein the disqualifying medical risk corresponds to a prediction drug taken by the applicant.

4. The method of claim 1, further comprising:

retrieving, by the processor, public data associated with the applicant of the electronic application, wherein the processor executes at least one of the first predictive model or the second predictive model using the public data retrieved.

5. The method of claim 1, wherein the explanation file comprises an explanation dashboard receives a selection input to select at least one variable of the plurality of variables of the electronic application.

6. The method of claim 5, wherein the explanation dashboard displays a graphical representation of marginal contribution of the at least one variable.

7. The method of claim 1, wherein the explanation file further includes a holistic explanation of a decision to decline the electronic application.

8. The method of claim 1, further comprising:

executing, by the processor, the explanation model that generates the explanation file including additive contributions of one or more of the plurality of variables of the electronic application, wherein the additive contributions quantify contributions of the one or more of the plurality of variables to a prediction by the explanation model.

9. The method of claim 8, wherein the explanation model executes at least one of a SHAP values (SHapley Additive exPlanation) algorithm, a Kernel SHAP (SHapley Additive exPlanation) algorithm, or a Tree SHAP (SHapley Additive exPlanation) algorithm.

10. The method of claim 1, wherein the first predictive model is trained by inputting a plurality of historical application records of an enterprise, wherein each historical application record is supplemented with public data identified with the applicant of the respective historical application record received from one or more third-party sources.

11. A non-transitory machine-readable storage medium having computer-executable instructions stored thereon that, when executed by one or more processors, cause the one or more processors to perform operations comprising:

receive a plurality of variables of an electronic application, the plurality of variables for the electronic application excluding clinical data for an applicant;

retrieve public data identified with the applicant of the electronic application;

execute, using the plurality of variables, a first predictive machine learning model by inputting selected features from the plurality of variables for the electronic application and the public data identified with the applicant of the electronic application to predict a mortality risk for the electronic application, wherein the first predictive machine learning model is trained by inputting a plurality of historical application records, wherein training the first predictive machine learning model comprises:

generating a set of model variables based on the plurality of historical application records;

iteratively training one or more models using the set of model variables and removing, in at least one subsequent iteration, at least a portion of the set of model variables based on a variable importance ranking for the set of model variables until the set of model variables converges; and training the first predictive machine learning model using the converged set of model variables;

execute, using the plurality of variables, a second predictive machine learning model to predict a propensity of the applicant of the electronic application to be a smoker;

determine, using predictions generated by the first predictive model and the second predictive model, a risk group for the electronic application;

execute an explanation model configured to generate an explanation file for display on a user interface, the explanation file including interpretability data based on determination of the risk group; and generate explanation data derived from the explanation file for display on a user interface, the explanation file including interpretability data based on determination of the risk group.

12. The non-transitory machine-readable storage medium of claim 11, wherein the instructions further cause the one or more processors to:

execute, using the plurality of variables, a third predictive model to predict a disqualifying medical risk associated with the electronic application, wherein the risk group further corresponds to the disqualifying medical risk.

13. The non-transitory machine-readable storage medium of claim 12, wherein the disqualifying medical risk corresponds to a prediction drug taken by the applicant.

14. The non-transitory machine-readable storage medium of claim 11, wherein the instructions further cause the one or more processors to:

retrieve public data associated with the applicant of the electronic application, wherein the processor executes at least one of the first predictive model or the second predictive model using the public data retrieved.

15. The non-transitory machine-readable storage medium of claim 11, wherein the explanation file comprises an explanation dashboard receives a selection input to select at least one variable of the plurality of variables of the electronic application.

16. The non-transitory machine-readable storage medium of claim 15, wherein the explanation dashboard displays a graphical representation of marginal contribution of the at least one variable.

17. The non-transitory machine-readable storage medium of claim 11, wherein the explanation file further includes a holistic explanation of a decision to decline the electronic application.

18. The non-transitory machine-readable storage medium of claim 11, wherein the instructions further cause the one or more processors to:

execute the explanation model that generates the explanation file including additive contributions of one or more of the plurality of variables of the electronic application, wherein the additive contributions quantify contributions of the one or more of the plurality of variables to a prediction by the explanation model.

19. The non-transitory machine-readable storage medium of claim 18, wherein the explanation model executes at least one of a SHAP values (SHapley Additive exPlanation) algorithm, a Kernel SHAP (SHapley Additive exPlanation) algorithm, or a Tree SHAP (SHapley Additive exPlanation) algorithm.

20. The non-transitory machine-readable storage medium of claim 11, wherein the first predictive model is trained by inputting a plurality of historical application records of an enterprise, wherein each historical application record is supplemented with public data identified with the applicant of the respective historical application record received from one or more third-party sources.

* * * * *